(12) United States Patent
Frank

(10) Patent No.: US 8,455,245 B2
(45) Date of Patent: Jun. 4, 2013

(54) ABCB5 POSITIVE MESENCHYMAL STEM CELLS AS IMMUNOMODULATORS

(75) Inventor: Markus H. Frank, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 392 days.

(21) Appl. No.: 11/809,790

(22) Filed: May 31, 2007

(65) Prior Publication Data
US 2008/0003206 A1 Jan. 3, 2008

Related U.S. Application Data

(60) Provisional application No. 60/809,407, filed on May 31, 2006.

(51) Int. Cl.
*C12N 5/0775* (2010.01)
*G01N 33/53* (2006.01)

(52) U.S. Cl.
USPC ............................................. 435/325; 435/7.1

(58) Field of Classification Search
USPC .................................................. 435/325, 7.1
See application file for complete search history.

(56) References Cited

U.S. PATENT DOCUMENTS

| | | | |
|---|---|---|---|
| 5,612,185 A | 3/1997 | Uhr et al. | |
| 5,906,934 A | 5/1999 | Grande et al. | |
| 6,355,239 B1 * | 3/2002 | Bruder et al. | 424/93.1 |
| 6,387,367 B1 | 5/2002 | Davis-Sproul et al. | |
| 6,464,983 B1 | 10/2002 | Grotendorst | |
| 6,541,024 B1 | 4/2003 | Kadiyala et al. | |
| 6,632,656 B1 | 10/2003 | Thomas et al. | |
| 6,797,269 B2 | 9/2004 | Mosca et al. | |
| 6,875,430 B2 | 4/2005 | McIntosh et al. | |
| 6,905,678 B2 | 6/2005 | Havenga et al. | |
| 7,029,666 B2 | 4/2006 | Bruder et al. | |
| 7,465,554 B2 | 12/2008 | Frank et al. | |
| 7,928,202 B2 | 4/2011 | Frank et al. | |
| 8,076,091 B2 | 12/2011 | Frank et al. | |
| 2007/0116691 A1 * | 5/2007 | Cambier et al. | 424/93.21 |
| 2008/0047026 A1 | 2/2008 | Fuchs et al. | |
| 2008/0118432 A1 | 5/2008 | Bergstein et al. | |
| 2009/0117117 A1 | 5/2009 | Frank et al. | |
| 2011/0165149 A1 | 7/2011 | Frank et al. | |
| 2011/0287034 A1 | 11/2011 | Frank et al. | |
| 2012/0034196 A1 | 2/2012 | Frank et al. | |

FOREIGN PATENT DOCUMENTS

| | | |
|---|---|---|
| EP | 0 174 810 A2 | 3/1986 |
| EP | 0 267 781 A2 | 5/1988 |
| WO | WO 93/25700 A1 | 12/1993 |
| WO | WO 01/98361 A2 | 12/2001 |
| WO | WO 02/040541 A2 | 5/2002 |
| WO | WO 2005/046762 A1 | 5/2005 |
| WO | WO 2005/068503 A2 | 7/2005 |

OTHER PUBLICATIONS

Frank et al. (2003) J. Biol. Chem., vol. 278 (47) 47156-47165.*
Shi et al. (2004) J. Radiat. Res., vol. 45, 19-24.*
Frassoni et al. (2003) Blood, vol. 102(3), 1138-1141.*
Adult Stem Cells 101, from http://stemcell.childrenshospital.org, pp. 1-5, printed Jun. 14, 2012.*
International Search Report for PCT/US2007/013022, mailing date Nov. 8, 2007.
Frank, N. et al., 2003, "Regulation of progenitor cell fusion by ABCB5 P-glycoprotein, a novel human ADP-binding cassette transporter," J Biol Chem, 278:47; 47156-47157.
Frank, N. et al. 2005, "ABCB5-mediated doxorubicin transport and chemoresistance in human malignant melanoma," Cancer Research, 65:10; 4320-4333.
Frank, N. et al. 2004, "ABCB5 P-glycoprotein is a molecular marker of the Hoechst 33342 side population phenotype among humal fetal skeletal muscle cells," FASEB Journal, 18:4-5; 144.9.
Frank, M. et al., 2004, "Immunomodulatory functions of mesenchymal stem cells," The Lancet, 363:9419; 1411-1412.
Jorgensen C. et al., 2003, "Engineering mesenchymal stem cells for immunotherapy,"Gene Therapy, 10:10; 928-931.
Shi C. et al., 2004, "Transplantation of dermal multipotent cells promotes the hematopoietic recovery in sublethally irradiated rats," J Radiation Res, 45:1; 19-24.
Young H. et al., 2005, "Adult-derived stem cells and their potential for use in tissue repair and molecular medicine," J Cellular and Molecular Med, 9:3; 753-769.
EMBL/GENBANK submission; NIH/NCBI; Accession No. O14573; Kalicki et al.; Mar. 1, 2002.
Bork et al., Go hunting in sequence databases but watch out for the traps. Trends Genet. Oct. 1996;12(10):425-7.
Bork, Powers and pitfalls in sequence analysis: the 70% hurdle. Genome Res. Apr. 2000;10(4):398-400.
Bowie et al., Deciphering the message in protein sequences: tolerance to amino acid substitutions. Science. Mar. 16, 1990;247(4948):1306-10.
Brenner, Errors in genome annotation. Trends Genet. Apr. 1999;15(4):132-3.
Dermer, Another Anniversary for the War on Cancer. Bio/Technology. Mar. 12, 1994. Available at http://virusmyth.com/aids/hiv/gdbiotech.htm. Last accessed Oct. 28, 2008. 2 pages.
Doerks et al., Protein annotation: detective work for function prediction. Trends Genet. Jun. 1998;14(6):248-50.
Frank et al., Specific MDR1 P-glycoprotein blockade inhibits human alloimmune T cell activation in vitro. J Immunol. Feb. 15, 2001;166(4):2451-9.
Freshney, Culture of Animal Cells: A Manual of Basic Technique. Alan R. Liss, Inc. New York. 1983:3-4.

(Continued)

*Primary Examiner* — Anne Marie S. Wehbe
(74) *Attorney, Agent, or Firm* — Wolf, Greenfield & Sacks, P.C.

(57) ABSTRACT

The present invention is directed to purified preparations of dermal mesenchymal stem cells that are characterized by the cell surface expression of the ABCB5 P-glycoprotein. The cells may be used for any purpose that mesenchymal stem cells from other course are used. For instance they may be administered to treat an organ transplant recipient to improve allograft survival or as a treatment to patients with autoimmune diseases such as multiple sclerosis and rheumatoid arthritis.

10 Claims, 9 Drawing Sheets

OTHER PUBLICATIONS

Georges et al, Detection of P-glycoprotein isoforms by gene-specific monoclonal antibodies. Proc Natl Acad Sci U S A. Jan. 1990;87(1):152-6.

Goodell et al., Isolation and functional properties of murine hematopoietic stem cells that are replicating in vivo. J Exp Med. Apr. 1, 1996;183(4):1797-806.

Knutsen et al., Cytogenetic and molecular characterization of random chromosomal rearrangements activating the drug resistance gene, MDR1/P-glycoprotein, in drug-selected cell lines and patients with drug refractory ALL. Genes Chromosomes Cancer. Sep. 1998;23(1):44-54.

Lazar et al., Transforming growth factor alpha: mutation of aspartic acid 47 and leucine 48 results in different biological activities. Mol Cell Biol. Mar. 1988;8(3):1247-52.

Mechetner et al., Efficient inhibition of P-glycoprotein-mediated multidrug resistance with a monoclonal antibody. Proc Natl Acad Sci U S A. Jul. 1, 1992;89(13):5824-8.

Menke et al., Expression analysis of multidrug efflux pump genes in mouse hematopoietic stem and progenitor cells. Blood. 1999;94(10)(Supp 1, Part 1):Abstract #132.

Mickley et al., Gene rearrangement: a novel mechanism for MDR-1 gene activation. J Clin Invest. Apr. 15, 1997;99(8):1947-57.

Pendse et al., P-Glycoprotein Functions as a Differentiation Switch in Antigen Presenting Cell Maturation. Am J Transplant. Dec. 2008; 6(12):2884-93.

Schatton et al., Identification of cells initiating human melanomas. Nature. Jan. 17, 2008; 451(7176):345-9.

Schatton et al., The Chemoresistance Mediator ABCB5 Identifies Melanoma Stem Cells. 14th SPORE Investigator's Workshop 2006. National Cancer Institute. 2006:92. Abstract 150.

Schoenlein et al., Double minute chromosomes carrying the human multidrug resistance 1 and 2 genes are generated from the dimerization of submicroscopic circular DNAs in colchicine-selected KB carcinoma cells. Mol Biol Cell. May 1992;3(5):507-20.

Scott et al., The Pendred syndrome gene encodes a chloride-iodide transport protein. Nat Genet. Apr. 1999;21(4):440-3.

Spangrude et al., Two mechanisms of discrimination between stem cells and progenitors by rhodamine-123: Mitochondrial activation and multi-drug resistance. Blood. 1995;86(1)(Supp 1):Abstract #1830.

Storms et al., Isolation of primitive human hematopoietic progenitors on the basis of aldehyde dehydrogenase activity. Proc Natl Acad Sci U S A. Aug. 3, 1999;96(16):9118-23.

Robert, Multidrug resistance in oncology: diagnostic and therapeutic approaches. Eur J Clin Invest. Jun. 1999;29(6):536-45.

Young et al., Human pluripotent and progenitor cells display cell surface cluster differentiation markers CD10, CD13, CD56, and MHC class-1. Proc Soc Exp Biol Med. May 1999;221(I):63-71.

Chaudhary et al., Expression and activity of P-glycoprotein, a multidrug efflux pump, in human hematopoietic stem cells. Cell. Jul. 12, 1991;66(1):85-94.

\* cited by examiner

ABCB5 POSITIVE MESENCHYMAL STEM CELLS AS IMMUNOMODULATORS

RELATED APPLICATIONS

This application claims priority under 35 U.S.C. §119(e) to U.S. Provisional Application Ser. No. 60/809,407, entitled "ABCB5 POSITIVE MESENCHYMAL STEM CELLS AS IMMUNOMODULATORS," filed on May 31, 2006, which is herein incorporated by reference in its entirety.

FEDERALLY SPONSORED RESEARCH

This invention was made with government support under grant numbers SPORE P50CA093683 awarded by the NIH. The government has certain rights in this invention.

FIELD OF INVENTION

The present invention is directed at ABCB5 positive immunomodulatory mesenchymal stem cells and to their use in the treatment of immune mediated disease.

BACKGROUND OF INVENTION

Stem cell-based immunomodulatory strategies are a new therapeutic frontier in clinical allotransplantation (Frank, et. al., *Lancet* 363:1411 (2004)). It has been found, for example, that adult bone marrow-derived mesenchymal stem cells (BM-MSC) can inhibit T cell proliferation in response to mitogens and alloantigens in vitro (Le Blanc, et al., *Scand. J. Immunol.* 57:11 (2003); Rasmusson, et al., *Exp. Cell Res.* 305:33 (2005)). Because of its easy accessibility, skin is a particularly attractive potential source of therapeutically useful stem cells. However, identification of molecular markers for the isolation and expansion of pure dermal stem cells is a significant problem and the specific biological effects of these cells are largely unknown.

Recently, a novel human ATP-binding cassette (ABC) transporter, ABCB5 P-glycoprotein, was cloned and it has been suggested that this protein may serve as a marker for the isolation of a subpopulation of stem cells (Frank, et. al., *J. Biol. Chem.* 278:47156 (2003); Frank, et al., *Cancer Res.* 65:4320 (2005); U.S. Pat. No. 6,846,883).

SUMMARY OF INVENTION

The present invention is based in part upon the discovery that dermal mesenchymal stem cells that express ABCB5 have immunomodulatory properties and can be useful for the treatment of immune mediated diseases. The ABCB5 protein is expressed on the surface of the stem cells and can be used both in their identification, e.g., using immunofluorescence, and purification, e.g., using antibodies immobilized on an inert substrate.

In an aspect, the invention is directed to a method of obtaining immunomodulatory dermal mesenchymal stem cells (dermal MSC) from a sample of human skin and then isolating ABCB5 positive cells from the sample. ABCB5 cells may be identified, for instance, by immunofluorescence using antibodies against the human protein and by other methods as well. In this regard, it should be noted that the full amino acid and gene sequences for human ABCB5 are known in the art (see GenBank Accession No. NM_178559 and NP_848654) and monoclonal antibodies specific for this protein have been previously described (see e.g. Frank, et al., *Cancer Res.* 65:4320-4333 (2005); Frank, et al., *J. Biol. Chem.* 278:47156-47165 (2003)). A preferred method for the isolation of ABCB5 positive cells is through the use of antibodies that specifically recognize this protein and which have been immobilized, e.g., on a bead or column packing. Once obtained, the cells can be cloned by limiting dilution and expanded using methods well known in the art (see the Examples section for further discussion). Purified ABCB5 dermal MSC may be administered to a subject for the purpose of modulating the activity of immunity-associated cells, e.g. for inhibiting the activation of T-lymphocytes. This can be accomplished, for instance, by intravenously injecting or infusing the subject with between $1 \times 10^7 - 1 \times 10^{10}$ cells.

In other aspects the invention relates to a method for modulating immune molecule expression in a cell of a subject by administering to a subject ABCB5 positive dermal mesenchymal stem cells in an effective amount to modulate immune molecule expression in cells of the subject. For instance, it is demonstrated herein that in vivo transplantation of ABCB5$^+$-derived dermal mesenchymal stem cells can inhibit an APC-expressed positive costimulatory signal critically involved in T cell activation. In some embodiments the subject is administered $1 \times 10^7 - 1 \times 10^{10}$ ABCB5 positive dermal mesenchymal stem cells by intravenous injection or infusion.

In other aspects of the invention a method for promoting allograft survival is provided. The method is achieved by administering to a subject having an organ transplant an effective amount of ABCB5 positive dermal mesenchymal stem cells to promote allograft survival. The ABCB5 positive dermal mesenchymal stem cells may be administered to the subject prior to, at the same time as or after the organ transplant. In some embodiments the allograft is a heart; a lung; a liver; or a kidney.

In some embodiments the ABCB5 positive dermal mesenchymal stem cells are syngeneic. In other embodiments the ABCB5 positive dermal mesenchymal stem cells are allogeneic, for instance the ABCB5 positive dermal mesenchymal stem cells may be autologous to a person that donated the organ or derived from a third party.

Treatment may be given as far as seven days in advance of transplantation and still be effective. Administration may be repeated at regular intervals, e.g., daily, weekly, or monthly, to further suppress immune cell activation and prevent rejection of transplanted organs. The cells may be administrated intravenously by injection or infusion and it is expected that a single treatment will involve the administration of between $1 \times 10^7$ and $1 \times 10^{10}$ cells and more typically, between $1 \times 10^8$ and $5 \times 10^9$ cells. This treatment may be either given alone or in conjunction with other treatments to promote graft acceptance, e.g., the administration of cyclosporine.

The ability to reduce the activity of immune cells will also prove useful in the treatment of other types of subjects as well. For example, the cells may be given as a treatment in autoimmune diseases such as: multiple sclerosis; rheumatoid arthritis; systemic lupus erythematosus, scleroderma psoriasis; myasthenia gravis; Grave's disease, Crohn's disease; and ulcerative colitis. In addition, the cells can be given for the treatment of graft-versus-host disease.

Thus, a method of treating autoimmune disease is provided according to another aspects of the invention. The method involves administering to a subject having autoimmune disease ABCB5 positive dermal mesenchymal stem cells in an effective amount to treat the autoimmune disease.

In other aspects the invention is a method of treating liver disease by administering to a subject having a liver disease ABCB5 positive dermal mesenchymal stem cells in an effective amount to treat the liver disease. In one embodiment the liver disease is hepatitis.

In yet other aspects the invention is a method of treating a neurodegenerative disease by administering to a subject having a neurodegenerative disease ABCB5 positive dermal mesenchymal stem cells in an effective amount to treat the neurodegenerative disease, wherein the neurodegenerative disease is associated with an immune response against host cells. In one embodiment the neurodegenerative disease is amyotrophic lateral sclerosis.

A method of treating cardiovascular disease is provided according to other aspects of the invention. The method involves administering to a subject having cardiovascular disease ABCB5 positive dermal mesenchymal stem cells in an effective amount to treat the cardiovascular disease, wherein the cardiovascular disease is associated with tissue remodeling. In one embodiment the cardiovascular disease is atherosclerosis. In another embodiment the cardiovascular disease is myocardial infarction.

A method for promoting tissue regeneration by identifying dermal mesenchymal stem cells as ABCB5 positive dermal mesenchymal stem cells and administering to a subject in need thereof the ABCB5 positive dermal mesenchymal stem cells in an effective amount to promote tissue regeneration is provided according to another aspect of the invention. In one embodiment the tissue is cartilage or bone.

In some embodiments of the methods described herein the ABCB5 positive dermal mesenchymal stem cells are syngeneic. In other embodiments the ABCB5 positive dermal mesenchymal stem cells are allogeneic. In yet other embodiments the ABCB5 positive dermal mesenchymal stem cells are non-autologous.

In some embodiments the ABCB5 positive dermal mesenchymal stem cells are administered to the subject by intravenous injection or infusion.

In other aspects the invention is an isolated preparation of immunomodulatory dermal mesenchymal stem cells characterized by the expression of ABCB5 on their cell surface. In some embodiments the stem cells are substantially pure. A prefilled injection vial, ampoule or infusion bag of in unit dose form, encompassing the isolated dermal mesenchymal stem cells is also provided. The injection vial, ampoule or infusion bag may comprises $1\times10^7$-$1\times10^{10}$ of the dermal mesenchymal stem cells. In other embodiments the injection vial, ampoule or infusion bag comprises 1×108-5×109 of the dermal mesenchymal stem cells.

A kit is provided according to other aspects of the invention. The kit includes the prefilled injection vial, ampoule or infusion bag or the isolated preparation of immunomodulatory dermal mesenchymal stem cells characterized by the expression of ABCB5 together with instructions on the administration of the dermal mesenchymal stem cells to either a subject that has undergone or is about to undergo an organ transplant, a subject having an autoimmune disease, a liver disease, a neurodegenerative disease, or a cardiovascular disease. Other kits may include reagents for isolating and purifying such cells.

According to some embodiments the ABCB5 positive dermal mesenchymal stem cells have an exogenous nucleic acid. The exogenous nucleic acid may be a vector.

Several methods are disclosed herein of administering to a subject a composition for treatment of a particular condition. It is to be understood that in each such aspect of the invention, the invention specifically includes, also, the composition for use in the treatment of that particular condition, as well as use of the composition for the manufacture of a medicament for the treatment of that particular condition.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

Figure 1A:
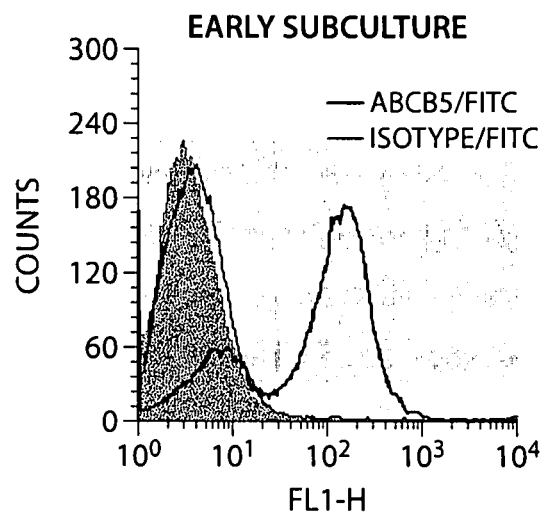
FIG. 1. Graphs depicting single-color flow cytometry analyses of surface ABCB5 expression of murine Balb/c skin-derived cultures in early subcultures (A) and after >40 subcultures (B). light gray line: ABCB5; shaded: isotype control; dark black line: unstained FIG. 2. A bar graph depicting the expression pattern of MSC markers on unseparated (solid bars) versus ABCB5⁻ (dotted bars) or ABCB5⁺ (striped bars) dermal MSC determined by dual-color flow cytometry.

Illustrated are mean values±SEM plotted against increasing stimulator to responder ratios. D. Bar graph depicting $^3$H-thymidine uptake of T cells derived from spleens of either MSC-treated (7 days post i.v. injection of $3\times10^6$ ABCB5$^+$ dermal MSC) (gray bar, labeled MSC Treatm) or untreated (black bar, labeled No Treatm.) C57BL6 mice upon mitogen (ConA)-stimulation for 72 hours. Illustrated are mean values±SEM.

DETAILED DESCRIPTION

The present invention is based in part upon the development of methods for isolating a subpopulation of dermal mesenchymal stem cells that are characterized by the expression of the P-glycoprotein ABCB5 on their cell surface and by the expression of the immune regulator PD-1. It has been found that ABCB5$^+$ dermal mesenchymal stem cells markedly prolong heterotopic murine cardiac allograft survival in vivo, and, with concurrent CD40-CD40L positive costimulatory pathway blockade, induce long-term allograft survival. The exact mechanism responsible for reducing immune rejection of transplanted organs has not been determined with certainty but it appears that the dermal stem cells express PD-1, a factor believed to inhibit T lymphocyte activation. The results obtained suggest that ABCB5$^+$ dermal mesenchymal stem cells are more effective as in vivo modulators of allograft rejection than bone marrow—mesenchymal stem cells (BM-MSC), which to date have been shown to induce only modest prolongation of allograft survival (Bartholomew, et al., *Exp. Hematol.* 30:42 (2002)) However, dermal mesenchymal stem cells may be otherwise comparable to BM-MSC in that they display a similar differentiation capacity and show a nearly identical profile with respect to other surface markers (Fernandes, et al., *Nat. Cell Biol.* 6:1082 (2004); Shih, et al., *Stem Cells* 23:1012 (2005)). The potential promise of clonal dermal mesenchymal stem cells for use in cell-based immunomodulatory therapeutic strategies in allotransplantation and the other diseases described herein is underscored by the additional advantage of easy accessibility of skin as a tissue source for stem cell isolation. The dermal mesenchymal stem cells described herein are easily isolated and expanded. ABCB5$^+$ dermal mesenchymal stem cells can be purified, cloned, propagated and expanded among clonally-derived differentiating cultures for greater than 50 passages.

Antigen-dependent T cell activation requires two distinct signals: on antigen encounter, naïve T cells receive signal 1 through T cell receptor engagement with the MHC-plus antigenic peptide complex, and signal 2 through positive costimulatory pathways leading to full activation. Negative T cell costimulatory signals, on the other hand, function to down-regulate immune responses (Rothstein, et al., *Immunol. Rev.* 196:85 (2003)). PD-1, a constituent of the novel PD-1-(PD-L1/PD-L2) negative costimulatory pathway (Carter, et al, *Eur. J. Immunol.* 32:634 (2002); Freeman, et al, *J. Exp. Med.* 192.1027 (2000); Ito, et al., *J. Immunol.* 174:6648 (2005)), has already been shown to be expressed on BM-MSC and to inhibit lymphocyte activation in vitro (Augello, et al., *Eur. J. Immunol.* 35:1482 (2005)). While not being held to any particular theory, it is believed that ABCB5$^+$ dermal mesenchymal stem cells may similarly function to down-regulate in vivo alloimmune responses via PD1-(PD-L1/PD-L2)-mediated negative costimulatory signaling, and that allografted ABCB5$^+$ dermal mesenchymal stem cells may therefore synergize with CD40-CD40L costimulatory blockade to further suppress allograft rejection compared to either therapy alone.

"ABCB5 positive dermal mesenchymal stem cells" as used herein refers to cells of the skin having the capacity to self-renew and to differentiate into mature cells of multiple adult cell lineages such as bone, fat and cartilage. These cells are characterized by the expression of ABCB5 on the cell surface. In culture, mesenchymal stem cells may be guided to differentiate into bone, fat, cartilage, or muscle cells using specific media. (Hirschi K K and, Goodell M A. *Gene Ther.* 2002; 9: 648-652. Pittenger M F, et al., *Science.* 1999; 284: 143-147. Schwartz R E, et al., *J. Clin Invest.* 2002; 109: 1291-1302. Hirschi K and Goodell M. *Differentiation.* 2001; 68: 186-192.)

Mesenchymal stem cells have been shown to exert immunoregulatory fuictions: For example, adult BM-MSC can inhibit T cell proliferation to cognate antigen, alloantigen and mitogen in vitro and attenuate graft-versus-host disease (GVHD), allograft rejection and cell-mediated autoimmunity in vivo. mesenchymal stem cells express MHC class I antigens and can be induced to express MHC class II molecules by exposure to interferon-γ, which indicates an ability to provide signal 1 in a proinflammatory environment. While mesenchymal stem cells do not express the positive costimulatory pathway members CD80, CD86, CD40, or CD40L to provide signal 2, they can express PD-1, a constituent of the novel PD-1-(PD-L1/PD-L2) negative costimulatory pathway, which, upon engagement to its ligands on target immune-competent cells, may be responsible for mesenchymal stem cells-mediated lymphocyte activation in vitro. These findings raise the possibility that allogeneic or autologous mesenchymal stem cells might exert their immunoregulatory effects at sites of inflammation via provision of inhibitory costimulatory signals to antigen-reactive T cells, because such signals can be provided in cis or trans leading to T-cell inactivation. In addition, mesenchymal stem cells might exert immunoregulatory effects and retain immunoprivilege in the inflammatory environment via secretion of soluble immunoregulatory mediators: Members of the TGF-β superfamily, which are produced by mesenchymal stem cells, can suppress T cell-mediated antigen responses in vitro, and production of bone morphogenetic protein 2 (BMP-2) by mesenchymal stem cells might mediate immunosuppression via the generation of CD8$^+$ TREGs. Therefore, several distinct mechanisms by which mesenchymal stem cells modulate immune response activation are likely operative, including induction of T and B cell anergy, inhibition of APC maturation as evidenced by CD40 down-regulation, and generation of TREGs.

The ABCB5 positive dermal mesenchymal stem cells can be obtained from skin. The skin may be derived from any subject having skin, but in some embodiments is preferably human skin. The skin may be derived from a subject of any age but in some embodiments is preferably adult skin, rather than adolescent or infant skin.

The ABCB5 positive dermal mesenchymal stem cells may be derived from a subject by isolating a sample of skin and then purifying the ABCB5 positive dermal mesenchymal stem cells. It will be apparent to those of ordinary skill in the art that skin can be enriched for cells having ABCB5 in a number of ways. For example, the cells can be selected for, via binding of the ABCB5 on the cell surface molecules with antibodies or other binding molecules. Examples of methods are set forth in the examples below. Skin samples can be obtained directly from a donor or retrieved from cryopreservative storage. The dermal mesenchymal stem cells may, for instance, be isolated using antibodies against ABCB5 and maintained in culture using standard methodology or frozen, e.g., in liquid nitrogen, for later use.

To study the immunomodulatory properties of murine ABCB5+ dermal mesenchymal stem cells, a protocol may be used for isolating, cloning, propagating, and expanding this stem cell population in vitro under defined medium conditions such as those in the examples below. Briefly, murine skin was harvested from adult Balb/c or C57BL/6 strain mice, dissected into small pieces and dissociated with collagenase, followed by isolation of ABCB5+ cells using anti-ABCB5 mAb, goat anti-mouse Ig-coated magnetic microbeads and MiniMACS separation columns, and subsequent cell cloning by limiting dilution. Surface expression of murine ABCB5 was determined in clonally-derived successive cell passages using immunofluorescence staining with anti-ABCB5 mab and flow cytometry.

The present invention contemplates any suitable method of employing monoclonal antibodies to separate mesenchymal stem cells from other cells. Accordingly, included in the present invention is a method of producing a population of mesenchymal stem cells comprising the steps of providing a cell suspension of skin containing mesenchymal stem cells; contacting the cell suspension with one or a combination of monoclonal antibodies which recognize an epitope, including ABCB5, on the mesenchymal stem cells; and separating and recovering from the cell suspension the cells bound by the monoclonal antibodies. The monoclonal antibodies may be linked to a solid-phase and utilized to capture mesenchymal stem cells from skin samples. The bound cells may then be separated from the solid phase by known methods depending on the nature of the antibody and solid phase.

Monoclonal based systems appropriate for preparing the desired cell population include magnetic bead/paramagnetic particle column utilizing antibodies for either positive or negative selection; separation based on biotin or streptavidin affinity; and high speed flow cytometric sorting of immunofluorescent-stained mesenchymal stem cells mixed in a suspension of other cells. Thus, the method of the present invention includes the isolation of a population of mesenchymal stem cells and enhancement using monoclonal antibodies raised against surface antigen ABCB5.

The ABCB5 positive dermal mesenchymal stem cells are preferably isolated. An "isolated ABCB5 positive dermal mesenchymal stem cell" as used here in refers to a preparation of cells that are placed into conditions other than their natural environment. The term "isolated" does not preclude the later use of these cells thereafter in combinations or mixtures with other cells or in an in vivo environment.

The ABCB5 positive dermal mesenchymal stem cells may be prepared as substantially pure preparations. The term "substantially pure" means that a preparation is substantially free of skin cells other than ABCB5 positive stem cells. For example, the ABCB5 cells should constitute at least 70 percent of the total cells present with greater percentages, e.g., at least 85, 90, 95 or 99 percent, being preferred. The cells may be packaged in a finished pharmaceutical container such as an injection vial, ampoule, or infusion bag along with any other components that may be desired, e.g., agents for preserving cells, or reducing bacterial growth. The composition should be in unit dosage form.

The ABCB5 positive dermal mesenchymal stem cells are useful for treating immune mediated diseases. Immune mediated diseases are diseases associated with a detrimental immune response, i.e., one that damages tissue. These diseases include but are not limited to transplantation, autoimmune disease, cardiovascular disease, liver disease, kidney disease and neurodegenerative disease.

It has been discovered that mesenchymal stem cells can be used in transplantation to ameliorate a response by the immune system such that an immune response to an antigen(s) will be reduced or eliminated. Transplantation is the act or process of transplanting a tissue or an organ from one body or body part to another. The mesenchymal stem cells may be autologous to the host (obtained from the same host) or non-autologous such as cells that are allogeneic or syngeneic to the host. Non-autologous cells are derived from someone other than the patient or the donor of the organ. Alternatively the mesenchymal stem cells can be obtained from a source that is xenogeneic to the host.

Allogeneic refers to cells that are genetically different although belonging to or obtained from the same species as the host or donor. Thus, an allogeneic human mesenchymal stem cell is a mesenchymal stem cell obtained from a human other than the intended recipient of the mesenchymal stem cells or the organ donor. Syngeneic refers to cells that are genetically identical or closely related and immunologically compatible to the host or donor, i.e., from individuals or tissues that have identical genotypes. Xenogeneic refers to cells derived or obtained from an organism of a different species than the host or donor.

Thus, the mesenchymal stem cells are used to suppress or ameliorate an immune response to a transplant (tissue, organ, cells, etc.) by administering to the transplant recipient mesenchymal stem cells in an amount effective to suppress or ameliorate an immune response against the transplant.

Accordingly, the methods may be achieved by contacting the recipient of donor tissue with mesenchymal stem cells. The mesenchymal stem cells can be administered to the recipient before or at the same time as the transplant or subsequent to the transplant. When administering the stem cells prior to the transplant, typically stem cells should be administered up to 14 days and preferably up to 7 days prior to surgery. Administration may be repeated on a regular basis thereafter (e.g., once a week).

The mesenchymal stem cells can also be administered to the recipient as part of the transplant. For instance, the mesenchymal stem cells may be perfused into the organ or tissue before transplantation. Alternatively the tissue may be transplanted and then treated during the surgery.

Treatment of a patient who has received a transplant, in order to reduce the severity of or eliminate a rejection episode against the transplant may also be achieved by administering to the recipient of donor tissue mesenchymal stem cells after the donor tissue has been transplanted into the recipient.

Reducing an immune response by donor tissue, organ or cells against a recipient, i.e. graft versus host response may be accomplished by treating the donor tissue, organ or cells with mesenchymal stem cells ex vivo prior to transplantation of the tissue, organ or cells into the recipient. The mesenchymal stem cells reduce the responsiveness of T cells in the transplant that may be subsequently activated against recipient antigen presenting cells such that the transplant may be introduced into the recipient's (host's) body without the occurrence of, or with a reduction in, an adverse response of the transplant to the host. Thus, what is known as "graft versus host" disease may be averted.

The mesenchymal stem cells can be obtained from the recipient or donor, for example, prior to the transplant. The mesenchymal stem cells can be isolated and stored frozen until needed. The mesenchymal stem cells may also be culture-expanded to desired amounts and stored until needed. Alternatively they may be obtained immediately before use.

The mesenchymal stem cells are administered to the recipient in an amount effective to reduce or eliminate an ongoing adverse immune response caused by the donor transplant against the host. The presentation of the mesenchymal stem cells to the host undergoing an adverse immune response caused by a transplant inhibits the ongoing response and prevents restimulation of the T cells thereby reducing or eliminating an adverse response by activated T cells to host tissue.

As part of a transplantation procedure the mesenchymal stem cells may also be modified to express a molecule to enhance the protective effect, such as a molecule that induces cell death. As described in more detail below, the dermal mesenchymal stem cells can be engineered to produce proteins using exogenously added nucleic acids. For instance, the mesenchymal stem cells can be used to deliver to the immune system a molecule that induces apoptosis of activated T cells carrying a receptor for the molecule. This results in the deletion of activated T lymphocytes and in the suppression of an unwanted immune response to a transplant. Thus, dermal mesenchymal stem cells may be modified to express a cell death molecule. In preferred embodiments of the methods described herein, the mesenchymal stem cells express the cell death molecule Fas ligand or TRAIL ligand.

In all cases an effective dose of cells (i.e., a number sufficient to prolong allograft survival should be given to a patient). The number of cells administered should generally be in the range of $1\times10^7$-$1\times10^{10}$ and, in most cases should be between $1\times10^8$ and $5\times10^9$. Actual dosages and dosing schedules will be determined on a case by case basis by the attending physician using methods that are standard in the art of clinical medicine and taking into account factors such as the patient's age, weight, and physical condition. In cases where a patient is exhibiting signs of transplant rejection, dosages and/or frequency of administration may be increased. The cells will usually be administered by intravenous injection or infusion although methods of implanting cells, e.g. near the site of organ implantation, may be used as well.

The mesenchymal stem cells may be administered to a transplant patient either as the sole immunomodulator or as part of a treatment plan that includes other immunomodulators as well. For example, patients may also be given: monoclonal antibodies or other compounds that block the interaction between CD40 and CD40L; inhibitors of lymphocyte activation and subsequent proliferation such as cyclosporine, tacrolimus and rapamycin; or with immunosuppressors that act by other mechanisms such as methotrexate, azathioprine, cyclophosphamide, or anti-inflammatory compounds (e.g., adrenocortical steroids such as dexamethasone and prednisolone).

The dermal mesenchymal stem cells of the invention are also useful for treating and preventing autoimmune disease. Autoimmune disease is a class of diseases in which an subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

A "self-antigen" as used herein refers to an antigen of a normal host tissue. Normal host tissue does not include cancer cells.

An example of autoimmune disease is anti-glomerular basement membrane (GBM) disease. GBM disease results from an autoimmune response directed against the noncollagenous domain 1 of the 3 chain of type IV collagen (3(IV) NC1) and causes a rapidly progressive glomerulonephritis (GN) and ultimately renal failure in afflicted patients. As described in the examples below the effectiveness of dermal mesenchymal stem cells in a model of GBM has been demonstrated. Autoreactive antibodies recognizing 3(IV)NC1 are considered hallmark of the disease. In addition, 3(IV)NC1-autoreactive T helper (Th)1-mediated cellular immunity has been implicated in its pathogenesis. Anti-GBM disease can be induced experimentally in susceptible mouse strains by immunization with antigen preparations containing recombinant 3(IV)NC1 (r3(IV)NC1), providing for a valuable disease model system to study responses to therapeutic immunomodulation. Antigen-dependent T cell activation and resultant production of interleukin 2 (IL-2) requires two distinct signals: On antigen encounter, naive T cells receive signal 1 through the T cell receptor engagement with the Major Histocompatibility Complex (MHC)-plus antigenic peptide complex on antigen presenting cells (APCs), and signal 2 through positive costimulatory pathways leading to full activation. The critical role of one such positive costimulatory pathway, the interaction of APC-expressed CD40 with its Th ligand CD40L, for disease development in experimental anti-GBM autoimmune GN has recently been demonstrated, and CD40-CD40L pathway blockade has been found to prevent the development of autoimmune autoimmune GN. Negative T cell costimulatory signals, on the other hand, function to down-regulate immune responses. Regulatory T cells (TREGs) and soluble cytokine mediators, such as interleukin 10 and members of the transforming growth factor β (TGF-β) family, can also attenuate T cell activation and immune effector responses.

Another autoimmune disease is Crohn's disease. Clinical trials for the treatment of Crohn's disease using mesenchymal stem cells have been conducted. Crohn's disease is a chronic condition associated with inflammation of the bowels and gastrointestinal tract. Based on the conducted trials the use of mesenchymal stem cells for the treatment of Crohn's disease appears promising.

When used in the treatment of an autoimmune disease, the ABCB5 positive dermal mesenchymal stem cells will preferably be administered by intravenous injection and an effective dose will be the amount needed to slow disease progression or alleviate one or more symptoms associated with the disease. For example, in the case of relapsing multiple sclerosis, an effective dose should be at least the amount needed to reduce the frequency or severity of attacks. In the case of rheumatoid arthritis, an effective amount would be at least the number of cells needed to reduce the pain and inflammation experienced by patients. A single unit dose of cells should typically be between $1\times10^7$ and $1\times10^{10}$ cells and dosing should be repeated at regular intervals (e.g., weekly, monthly etc.) as determined to be appropriate by the attending physician.

The ABCB5 positive dermal mesenchymal stem cells are also useful in the treatment of liver disease. Liver disease includes disease such as hepatitis which result in damage to liver tissue. More generally, the ABCB5 positive dermal mesenchymal stem cells of the present invention can be used for the treatment of hepatic diseases, disorders or conditions including but not limited to: alcoholic liver disease, hepatitis (A, B, C, D, etc.), focal liver lesions, primary hepatocellular carcinoma, large cystic lesions of the liver, focal nodular hyperplasia granulomatous liver disease, hepatic granulomas, hemochromatosis such as hereditary hemochromatosis, iron overload syndromes, acute fatty liver, hyperemesis gravidarum, intercurrent liver disease during pregnancy, intrahepatic cholestasis, liver failure, fulminant hepatic failure, jaundice or asymptomatic hyperbilirubinemia, injury to hepatocytes, Crigler-Najjar syndrome, Wilson's disease, alpha-1-antitrypsin deficiency, Gilbert's syndrome, hyperbilirubinemia, nonalcoholic steatohepatitis, porphyrias, noncirrhotic portal hypertension, noncirrhotic portal hypertension, portal fibrosis, schistosomiasis, primary biliary cirrhosis, Budd-Chiari syndrom, hepatic veno-occlusive disease following bone marrow transplantation, etc.

Stress on the body can trigger adult stem cells to change into specialized cells that migrate to the damaged area and help repair the injury. For example, a damaged liver can send signals to stem cells which respond by creating liver cells for the damaged liver. (Journal of Clinical Investigation 2003 Jul. 15; 112 (2):160-169)

In some embodiments, the invention is directed to treating a neurodegenerative disease, with dermal mesenchymal stem cells. In some cases, the invention contemplates the treatment of subjects having neurodegenerative disease, or an injury to nerve cells which may lead to neuro-degeneration. Neuronal cells are predominantly categorized based on their local/regional synaptic connections (e.g., local circuit interneurons vs. longrange projection neurons) and receptor sets, and associated second messenger systems. Neuronal cells include both central nervous system (CNS) neurons and peripheral nervous system (PNS) neurons. There are many different neuronal cell types. Examples include, but are not limited to, sensory and sympathetic neurons, cholinergic neurons, dorsal root ganglion neurons, proprioceptive neurons (in the trigeminal mesencephalic nucleus), ciliary ganglion neurons (in the parasympathetic nervous system), etc. A person of ordinary skill in the art will be able to easily identify neuronal cells and distinguish them from non-neuronal cells such as glial cells, typically utilizing cell-morphological characteristics, expression of cell-specific markers, secretion of certain molecules, etc.

"Neurodegenerative disorder" or "neurodegenerative disease" is defined herein as a disorder in which progressive loss of neurons occurs either in the peripheral nervous system or in the central nervous system. Non-limiting examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor), and Wernicke-Korsakoff's related dementia. Neurodegenerative diseases affecting sensory neurons include Friedreich's ataxia, diabetes, peripheral neuropathy, and retinal neuronal degeneration. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder" or "neurodegenerative disease".

Most of the chronic neurodegenerative diseases are typified by onset during the middle adult years and lead to rapid degeneration of specific subsets of neurons within the neural system, ultimately resulting in premature death. Compositions comprising dermal mesenchymal stem cells may be administered to a subject to treat neurodegenerative disease alone or in combination with the administration of other therapeutic compounds for the treatment or prevention of these disorders or diseases. Many of these drugs are known in the art. For example, antiparkinsonian agents include but are not limited to Benztropine Mesylate; Biperiden; Biperiden Hydrochloride; Biperiden Lactate; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinelorane Hydrochloride; Ropinirole Hydrochloride; Selegiline Hydrochloride; Tolcapone; Trihexyphenidyl Hydrochloride. Drugs for the treatment of amyotrophic lateral sclerosis include but are not limited to Riluzole. Drugs for the treatment of Paget's disease include but are not limited to Tiludronate Disodium.

The utility of adult stem cells in the treatment of neurodegenerative disease has been described. It has been demonstrated that mesenchymal stem cells can change into neuron-like cells in mice that have experienced strokes. Journal of Cell Transplantation Vol. 12, pp. 201-213, 2003. Additionally, stem cells derived from bone marrow developed into neural cells that hold promise to treat patients with Parkinson's disease, amyotrophic lateral sclerosis (ALS), and spinal cord injuries.

The methods of the invention are also useful in the treatment of disorders associated with kidney disease. Mesenchymal stem cells previously injected into kidneys have been demonstrated to result in an almost immediate improvement in kidney function and cell renewal. Resnick, Mayer, Stem Cells Brings Fast Direct Improvement, Without Differentiation, in Acute Renal Failure, EurekAlert!, Aug. 15, 2005. Thus, the dermal mesenchymal stem cells of the invention may be administered to a subject having kidney disease alone or in combination with other therapeutics or procedures, such as dialysis, to improve kidney function and cell renewal.

Other diseases which may be treated according to the methods of the invention include diseases of the cornea and lung. Therapeis based on the adminstration of mesenchymal stem cells in these tissues have demonstrated positive results. For instance, human mesenchymal stem cells have been used to reconstruct damaged corneas. Ma Y et al, Stem Cells, Aug. 18, 2005. Additionally stem cells derived from bone marrow were found to be important for lung repair and protection against lung injury. Rojas, Mauricio, et al., American Journal of Respiratory Cell and Molecular Biology, Vol. 33, pp. 145-152, May 12, 2005. Thus the dermal mesenchymal stem cells of the invention may also be used in the repair of corneal tissue or lung tissue.

Mesenchymal stem cells from sources such as bone marrow have also been used in therapies for the treatment of cardiovascular disease. Bone marrow stem cells can help repair damaged heart muscle by helping the heart develop new, functional tissue. Goodell M A, Jackson K A, Majka S M, Mi T, Wang H, Pocius J, Hartley C J, Majesky M W, Entman M L, Michael L H, Hirschi K K. Stem cell plasticity in muscle and bone marrow. Ann NY Acad Sci. 2001 June; 938:208-18. Bone marrow stem cells placed in damaged hearts after myocaridal infarction improved the hearts' pumping ability by 80%. Nature Medicine Journal September 2003 vol. 9 no. 9: 1195-1201.

Cardiovascular disease refers to a class of diseases that involve the heart and/or blood vessels. While the term technically refers to diseases that affects the the heart and/or blood vessels, other organs such as, for example, the lungs, and joints might be affected or involved in the disease. Examples of cardiovasular diseases include, but are not limited to athersclerosis, arteriosclerosis, aneurysms, angina, chronic stable angina pectoris, unstable angina pectoris, myocardial ischemia (MI), acute coronary syndrome, coronary artery disease, stroke, coronary re-stenosis, coronary stent re-stenosis, coronary stent re-thrombosis, revascularization, post myocardial infarction (MI) remodeling (e.g., post MI remodeling of the left ventricle), post MI left ventricular hypertrophy, angioplasty, transient ischemic attack, pulmonary embolism, vascular occlusion, venous thrombosis, arrhythmias, cardiomyopathies, congestive heart failure, congenital heart disease, myocarditis, valve disease, dialated cardiomyopathy, diastolic dysfunction, endocarditis, rheumatic fever, hypertension (high blood pressure), hypertrophic cardiomyopathy, anneurysms, and mitral valve prolapse.

Atherosclerosis is a disease of large and medium-sized muscular arteries and is characterized by endothelial dysfunction, vascular inflammation, and the buildup of lipids, cholesterol, calcium, and/or cellular debris within the intimal layer of the blood vessel wall. This buildup results in plaque (atheromatous plaque) formation, vascular remodeling, acute and chronic luminal obstruction, abnormalities of blood flow, and diminished oxygen supply to target organs.

Atherosclerosis may cause two main problems First, the atheromatous plaques may lead to plaque ruptures and stenosis (narrowing) of the artery and, therefore, an insufficient blood supply to the organ it feeds. Alternatively, an aneurysm results. These complications are chronic, slowly progressing and cumulative. Most commonly, plaque(s) suddenly ruptures ("vulnerable plaque") causing the formation of a thrombus that will rapidly slow or stop blood flow (e.g., for a few minutes) leading to death of the tissues fed by the artery. This event is called an infarction. One of the most common recognized scenarios is called coronary thrombosis of a coronary artery causing myocardial infarction (MI) (commonly known as a heart attack). Another common scenario in very advanced disease is claudication from insufficient blood supply to the legs, typically due to a combination of both stenosis and aneurysmal segments narrowed with clots. Since atherosclerosis is a body wide process, similar events also occur in the arteries to the brain, intestines, kidneys, legs, etc.

Atherosclerosis may begin in adolescence, and is usually found in most major arteries, yet is asymptomatic and not detected by most diagnostic methods during life. It most commonly becomes seriously symptomatic when interfering with the coronary circulation supplying the heart or cerebral circulation supplying the brain, and is considered the most important underlying cause of strokes, heart attacks, various heart diseases including congestive heart failure and most cardiovascular diseases in general. Though any artery in the body can be involved, usually only severe narrowing or obstruction of some arteries, those that supply more critically-important organs are recognized. Obstruction of arteries supplying the heart muscle result in a heart attack. Obstruction of arteries supplying the brain result in a stroke. Atheromatous palque(s) in the arm or leg arteries producing decreased blood flow cause peripheral artery occlusive disease (PAOD)

Cardiac stress testing is one of the most commonly performed non-invasive testing method for blood flow limitation. It generally detects lumen narrowing of 75% or greater. Areas of severe stenosis detectable by angiography, and to a lesser extent "stress testing" have long been the focus of human diagnostic techniques for cardiovascular disease, in general. Most severe events occur in locations with heavy plaque. Plaque rupture can lead to artery lumen occlusion within seconds to minutes, and potential permanent tissue damage and sometimes sudden death.

Various anatomic, physiological and behavioral risk factors for atherosclerosis are known. These risk factors include advanced age, male gender, diabetes, dyslipidemia (elevated serum cholesterol or triglyceride levels), high serum concentration of low density lipoprotein (LDL, "bad cholesterol"), Lipoprotein(a) (a variant of LDL), and/or very low density lipoprotein (VLDL) particles, low serum concentration of functioning high density lipoprotein (HDL, "good cholesterol") particles, tobacco smoking, hypertension, obesity (e.g., central obesity, also referred to as abdominal or male-type obesity), family history of cardiovascular diease (eg. coronary heart disease or stroke), elevated levels of inflammatory markers (e.g., C-reactive protein (CRP or hs-CRP), sCD40L, sICAM, etc.), elevated serum levels of homocysteine, elevated serum levels of uric acid, and elevated serum fibrinogen concentrations.

The term myocardial infarction (MI) is derived from myocardium (the heart muscle) and infarction (tissue death due to oxygen starvation). MI is a disease state that occurs when the blood supply to a part of the heart is interrupted. Acute MI (AMI) is a type of acute coronary syndrome, which is most frequently (but not always) a manifestation of coronary artery disease. The most common triggering event is the disruption of an atherosclerotic plaque in an epicardial coronary artery, which leads to a clotting cascade, sometimes resulting in total occlusion of the artery. The resulting ischemia or oxygen shortage causes damage and potential death of heart tissue.

Important risk factors for MI or AMI include a previous history of vascular disease such as atherosclerotic coronary heart disease and/or angina, a previous heart attack or stroke, any previous episodes of abnormal heart rhythms or syncope, older ag (e.g., men over 40 and women over 50), tobacco smoking, excessive alcohol consumption, high triglyceride levels, high LDL ("Low-density lipoprotein") and low HDL ("High density lipoprotein"), diabetes, hypertension, obesity, and stress.

Symptoms of of MI or AMI include chest pain, shortness of breath, nausea, vomiting, palpitations, sweating, and anxiety or a feeling of impending doom. Subjects frequently feel suddenly ill. Approximately one third of all myocardial infarctions are silent, without chest pain or other symptoms.

A subject suspected of having a MI receives a number of diagnostic tests, such as an electrocardiogram (ECG, EKG), a chest X-ray and blood tests to detect elevated creatine kinase (CK) or troponin levels (markers released by damaged tissues, especially the myocardium). A coronary angiogram allows to visualize narrowings or obstructions on the heart vessels.

Myocardial infarction causes irreversible loss of heart muscle cells leading to a thin fibrotic scar that cannot contribute to heart function. Stem cell therapy provides a possible approach to the treatment of heart failure after myocardial infarction as well as atherosclerosis associated with remodeling. The basic concept of stem cell therapy is to increase the number of functional heart muscle cells by injecting immature heart muscle cells directly into the wall of the damaged heart. Myocardial infarction leads to the loss of cardiomyocytes, followed by pathological remodeling and progression to heart failure. One goal of stem cell therapy is to replace cardiomyocytes lost after ischemia, induce revascularization of the injured region. Another goal is to prevent deleterious pathological remodeling after myocardial infarction and associated with atheroschlerosis. Autologous or allogeneic mesenchymal stem cells are considered to be one of the potential cell sources for stem cell therapy. Thus, the dermal mesenchymal stem cells of the invention may be used in the treatment of cardiovascular diseases.

Another use for the dermal mesenchymal stem cells of the invention is in tissue regeneration. In this aspect of the invention, the ABCB5 positive cells are used to generate tissue by induction of differentiation. Isolated and purified mesenchymal stem cells can be grown in an undifferentiated state through mitotic expansion in a specific medium. These cells can then be harvested and activated to differentiate into bone, cartilage, and various other types of connective tissue by a number of factors, including mechanical, cellular, and biochemical stimuli. Human mesenchymal stem cells possess the potential to differentiate into cells such as osteoblasts and chondrocytes, which produce a wide variety of mesenchymal tissue cells, as well as tendon, ligament and dermis, and this potential is retained after isolation and for several population expansions in culture. Thus, by being able to isolate, purify, greatly multiply, and then activate mesenchymal stem cells to differentiate into the specific types of mesenchymal cells desired, such as skeletal and connective tissues such as bone, cartilage, tendon, ligament, muscle, and adipose, a process exists for treating skeletal and other connective tissue disorders. The term connective tissue is used herein to include the tissues of the body that support the specialized elements, and includes bone, cartilage, ligament, tendon, stroma, muscle and adipose tissue.

The methods and devices of the invention utilize isolated dermal mesenchymal progenitor cells which, under certain conditions, can be induced to differentiate into and produce different types of desired connective tissue, such as into bone or cartilage forming cells.

In another aspect, the present invention relates to a method for repairing connective tissue damage. The method comprises the steps of applying the dermal mesenchymal stem to an area of connective tissue damage under conditions suitable for differentiating the cells into the type of connective tissue necessary for repair.

The term "connective tissue defects" refers to defects that include any damage or irregularity compared to normal connective tissue which may occur due to trauma, disease, age, birth defect, surgical intervention, etc. Connective tissue defects also refers to non-damaged areas in which bone formation is solely desired, for example, for cosmetic augmentation.

The dermal mesenchymal stem cells may be administered directly to a subject by any known mode of administration or may be seeded onto a matrix or implant. Matrices or implants include polymeric matrices such as fibrous or hydrogel based devices. Two types of matrices are commonly used to support the mesenchymal stem cells as they differentiate into cartilage or bone. One form of matrix is a polymeric mesh or sponge; the other is a polymeric hydrogel. The matrix may be biodegradeable or nonbiodegradeable. The term biodegradable, as used herein, means a polymer that dissolves or degrades within a period that is acceptable in the desired application, less than about six months and most preferably less than about twelve weeks, once exposed to a physiological solution of pH 6-8 having a temperature of between about 25° C. and 38° C. A matrix may be biodegradable over a time period, for instance, of less than a year, more preferably less than six months, most preferably over two to ten weeks.

Fibrous matrices can be manufactured or constructed using commercially available materials. The matrices are typically formed of a natural or a synthetic polymer. Biodegradable polymers are preferred, so that the newly formed cartilage can maintain itself and function normally under the load-bearing present at synovial joints. Polymers that degrade within one to twenty-four weeks are preferable. Synthetic polymers are preferred because their degradation rate can be more accurately determined and they have more lot to lot consistency and less immunogenicity than natural polymers. Natural polymers that can be used include proteins such as collagen, albumin, and fibrin; and polysaccharides such as alginate and polymers of hyaluronic acid. Synthetic polymers include both biodegradable and non-biodegradable polymers. Examples of biodegradable polymers include polymers of hydroxy acids such as polylactic acid (PLA), polyglycolic acid (PGA), and polylactic acid-glycolic acid (PLGA), polyorthoesters, polyanhydrides, polyphosphazenes, and combinations thereof. Non-biodegradable polymers include polyacrylates, polymethacrylates, ethylene vinyl acetate, and polyvinyl alcohols. These should be avoided since their presence in the cartilage will inevitably lead to mechanical damage and breakdown of the cartilage.

In the preferred embodiment, the polymers form fibers which are intertwined, woven, or meshed to form a matrix having an interstitial spacing of between 100 and 300 microns. Meshes of polyglycolic acid that can be used can be obtained from surgical supply companies such as Ethicon, N.J. Sponges can also be used. As used herein, the term "fibrous" refers to either a intertwined, woven or meshed matrix or a sponge matrix.

The matrix is preferably shaped to fill the defect. In most cases this can be achieved by trimming the polymer fibers with scissors or a knife; alternatively, the matrix can be cast from a polymer solution formed by heating or dissolution in a volatile solvent.

The mesenchymal stem cells are seeded onto the matrix by application of a cell suspension to the matrix. This can be accomplished by soaking the matrix in a cell culture container, or injection or other direct application of the cells to the matrix.

The matrix seeded with cells is implanted at the site of the defect using standard surgical techniques. The matrix can be seeded and cultured in vitro prior to implantation, seeded and immediately implanted, or implanted and then seeded with cells. In the preferred embodiment, cells are seeded onto and into the matrix and cultured in vitro for between approximately sixteen hours and two weeks. It is only critical that the cells be attached to the matrix. Two weeks is a preferred time for culture of the cells, although it can be longer. Cell density at the time of seeding or implantation should be approximately 25,000 cells/mm$^3$.

Polymers that can form ionic or covalently crosslinked hydrogels which are malleable are used to encapsulate cells. For example, a hydrogel is produced by cross-linking the anionic salt of polymer such as alginic acid, a carbohydrate polymer isolated from seaweed, with calcium cations, whose strength increases with either increasing concentrations of calcium ions or alginate. The alginate solution is mixed with the cells to be implanted to form an alginate suspension. Then the suspension is injected directly into a patient prior to hardening of the suspension. The suspension then hardens over a short period of time due to the presence in vivo of physiological concentrations of calcium ions.

The polymeric material which is mixed with cells for implantation into the body should form a hydrogel. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™. or Tetronics™., polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly (phosphazenes), poly(acrylic acids), poly(methacrylic acids), copolymers of acrylic acid and methacrylic acid, poly (vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Polymers can be synthesized that degrade by hydrolysis by incorporating monomers having imidazole, amino acid ester, or glycerol side groups. For example, a polyanionic poly[bis(carboxylatophenoxy)]phosphazene (PCPP) can be synthesized, which is cross-linked with dissolved multivalent cations in aqueous media at room temperature or below to form hydrogel matrices.

The water soluble polymer with charged side groups is ionically crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, zinc, and tin, although di-, trior tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

Preferably the polymer is dissolved in an aqueous solution, preferably a 0.1 M potassium phosphate solution, at physiological pH, to a concentration forming a polymeric hydrogel, for example, for alginate, of between 0.5 to 2% by weight, preferably 1%, alginate. The isolated cells are suspended in the polymer solution to a concentration of between 1 and 10 million cells/ml, most preferably between 10 and 20 million cells/ml.

In an embodiment, the cells are mixed with the hydrogel solution and injected directly into a site where it is desired to implant the cells, prior to hardening of the hydrogel. However, the matrix may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. One could also apply an external mold to shape the injected solution. Additionally, by controlling the rate of polymerization, it is possible to mold the cell-hydrogel injected implant Alternatively, the mixture can be injected into a mold, the hydrogel allowed to harden, then the material implanted.

The suspension can be injected via a syringe and needle directly into a specific area wherever a bulking agent is desired, especially soft tissue defects. The suspension can also be injected as a bulking agent for hard tissue defects, such as bone or cartilage defects, either congenital or acquired disease states, or secondary to trauma, burns, or the like. An example of this would be an injection into the area surrounding the skull where a bony deformity exists secondary to trauma. The injection in these instances can be made directly into the needed area with the use of a needle and syringe under local or general anesthesia.

The dermal mesenchymal stem cells may be modified to express proteins which are also useful in the therapeutic indications, as described in more detail below. For example, the cells may include a nucleic acid that produces at least one bioactive factor which further induces or accelerates the differentiation of the mesenchymal stem cells into a differentiated lineage. In the instance that bone is being formed, the bioactive factor may be a member of the TGF-beta superfamily comprising various tissue growth factors, particularly bone morphogenic proteins, such as at least one selected from the group consisting of BMP-2, BMP-3, BMP-4, BMP-6 and BMP-7.

The cells of the invention may be useful in a method for inducing T cell anergy, in vitro. Induction of T cell anergy involves culturing the dermal mesenchymal stem cells in the presence of antigen under conditions sufficient to induce the formation of T cells and/or T cell progenitors and to inhibit activation of the formed T cells and/or T cell progenitors. Anergy is defined as an unresponsive state of T cells (that is they fail to produce IL-2 on restimulation, or proliferate when restimulated) (Zamoyska R, Curr Opin Immunol, 1998, 10(1):82-87; Van Parijs L, et al., Science, 1998, 280(5361): 243-248; Schwartz R H, Curr Opin Immunol, 1997, 9(3):351-357; Immunol Rev, 1993, 133:151-76). Anergy can be measured by taking the treated T cells and restimulating them with antigen in the presence of APCs. If the cells are anergic they will not respond to antigen at an appropriate concentration in the context of APCs.

As used herein, a subject is a human, non-human primate, cow, horse, pig, sheep, goat, dog, cat or rodent. Human dermal mesenchymal stem cells and human subjects are particularly important embodiments.

In a still further aspect of the invention described herein, mesenchymal stem cells may be genetically engineered (or transduced or transfected) with a gene of interest. The transduced cells can be administered to a patient in need thereof, for example to treat genetic disorders or diseases.

The ABCB5 positive dermal mesenchymal stem cells, and progeny thereof, can be genetically altered. Genetic alteration of a ABCB5 positive dermal mesenchymal stem cell includes all transient and stable changes of the cellular genetic material which are created by the addition of exogenous genetic material. Examples of genetic alterations include any gene therapy procedure, such as introduction of a functional gene to replace a mutated or nonexpressed gene, introduction of a vector that encodes a dominant negative gene product, introduction of a vector engineered to express a ribozyme and introduction of a gene that encodes a therapeutic gene product. Natural genetic changes such as the spontaneous rearrangement of a T cell receptor gene without the introduction of any agents are not included in this concept. Exogenous genetic material includes nucleic acids or oligonucleotides, either natural or synthetic, that are introduced into the dermal mesenchymal stem cells. The exogenous genetic material may be a copy of that which is naturally present in the cells, or it may not be naturally found in the cells. It typically is at least a portion of a naturally occurring gene which has been placed under operable control of a promoter in a vector construct.

Various techniques may be employed for introducing nucleic acids into cells. Such techniques include transfection of nucleic acid-CaPO$_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid according to the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

One method of introducing exogenous genetic material into the dermal mesenchymal stem cells is by transducing the cells using replication-deficient retroviruses. Replication-deficient retroviruses are capable of directing synthesis of all virion proteins, but are incapable of making infectious particles. Accordingly, these genetically altered retroviral vectors have general utility for high-efficiency transduction of genes in cultured cells. Retroviruses have been used extensively for transferring genetic material into cells. Standard protocols for producing replication-deficient retroviruses (including the steps of incorporation of exogenous genetic material into a plasmid, transfection of a packaging cell lirie with plasmid, production of recombinant retroviruses by the packaging cell line, collection of viral particles from tissue culture media, and infection of the target cells with the viral particles) are provided in the art.

The major advantage of using retroviruses is that the viruses insert efficiently a single copy of the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types. The major disadvantages of using a retrovirus expression vector are (1) insertional mutagenesis, i.e., the insertion of the therapeutic gene into an undesirable position in the target cell genome which, for example, leads to unregulated cell growth and (2) the need for target cell proliferation in order for the therapeutic gene carried by the vector to be integrated into the target genome. Despite these apparent limitations, delivery of a therapeutically effective amount of a therapeutic agent via a retrovirus can be efficacious if the efficiency of transduction is high and/or the number of target cells available for transduction is high.

Yet another viral candidate useful as an expression vector for transformation of dermal mesenchymal stem cells is the adenovirus, a double-stranded DNA virus. Like the retrovirus, the adenovirus genome is adaptable for use as an expression vector for gene transduction, i.e., by removing the genetic information that controls production of the virus itself. Because the adenovirus functions usually in an extra-chromosomal fashion, the recombinant adenovirus does not have the theoretical problem of insertional mutagenesis. On the other hand, adenoviral transformation of a target dermal mesenchymal stem cell may not result in stable transduction.

However, more recently it has been reported that certain adenoviral sequences confer intrachromosomal integration specificity to carrier sequences, and thus result in a stable transduction of the exogenous genetic material.

Thus, as will be apparent to one of ordinary skill in the art, a variety of suitable vectors are available for transferring exogenous genetic material into dermal mesenchymal stem cells. The selection of an appropriate vector to deliver a therapeutic agent for a particular condition amenable to gene replacement therapy and the optimization of the conditions for insertion of the selected expression vector into the cell, are within the scope of one of ordinary skill in the art without the need for undue experimentation. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any nontranslated DNA sequence which works contiguous with the coding sequence (in cis) to change the basal transcription level dictated by the promoter. Preferably, the exogenous genetic material is introduced into the dermal mesenchymal stem cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann et al., *Proc. Natl. Acad. Sci.* USA 88:4626-4630 (1991)), adenosine deaminase, phosphoglycerol kinase (PGK), pyruvate kinase, phosphoglycerol mutase, the actin promoter (Lai et al., *Proc. Natl. Acad. Sci.* USA 86: 10006-10010 (1989)), and other constitutive promoters known to those of skill in the art. In addition, many viral promoters function constitutively in eukaryotic cells. These include: the early and late promoters of SV40; the long terminal repeats (LTRS) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified dermal mesenchymal stem cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the subject.

In addition to at least one promoter and at least one heterologous nucleic acid encoding the therapeutic agent, the expression vector preferably includes a selection gene, for example, a neomycin resistance gene, for facilitating selection of dermal mesenchymal stem cells that have been transfected or transduced with the expression vector. Alternatively, the dermal mesenchymal stem cells are transfected with two or more expression vectors, at least one vector containing the gene(s) encoding the therapeutic agent(s), the other vector containing a selection gene. The selection of a suitable promoter, enhancer, selection gene and/or signal sequence is deemed to be within the scope of one of ordinary skill in the art without undue experimentation.

The selection and optimization of a particular expression vector for expressing a specific gene product in an isolated dermal mesenchymal stem cell is accomplished by obtaining the gene, preferably with one or more appropriate control regions (e.g., promoter, insertion sequence); preparing a vector construct comprising the vector into which is inserted the gene; transfecting or transducing cultured dermal mesenchymal stem cells in vitro with the vector construct; and determining whether the gene product is present in the cultured cells.

Thus, the present invention makes it possible to genetically engineer dermal mesenchymal stem cells in such a manner that they produce polypeptides, hormones and proteins not normally produced in human stem cells in biologically significant amounts or produced in small amounts but in situations in which overproduction would lead to a therapeutic benefit. These products would then be secreted into the bloodstream or other areas of the body, such as the central nervous system. The human stem cells formed in this way can serve as a continuous drug delivery systems to replace present regimens, which require periodic administration (by ingestion, injection, depot infusion etc.) of the needed substance. This invention has applicability in providing hormones, enzymes and drugs to humans, in need of such substances. It is particularly valuable in providing such substances, such as hormones (e.g., parathyroid hormone, insulin), which are needed in sustained doses for extended periods of time.

For example, it can be used to provide continuous delivery of insulin, and, as a result, there would be no need for daily injections of insulin. Genetically engineered human mesenchymal stem cells can also be used for the production of clotting factors such as Factor VIII, or for continuous delivery of dystrophin to muscle cells for muscular dystrophy.

Incorporation of genetic material of interest into dermal mesenchymal stem cells is particularly valuable in the treatment of inherited and acquired disease. In the case of inherited diseases, this approach is used to provide genetically modified human mesenchymal stem cells and other cells which can be used as a metabolic sink. That is, such dermal mesenchymal stem cells would serve to degrade a potentially toxic substance. For example, this could be used in treating disorders of amino acid catabolism including the hyperphenylalaninemias, due to a defect in phenylalanine hydroxylase; the homocysteinemias, due to a defect in cystathionine beta-synthase.

The dermal mesenchymal stem cells may further be modified to express a cell death molecule to enhance the elimination of activated T cells, in the treatment of organ or tissue transplantation. For example, the cell death molecule may be expressed by the mesenchymal stem cells which have been engineered to express the exogenous cell death molecule. As used herein, a "cell death molecule" is a molecule that interacts or binds with its cognate receptor on a stimulated T cell inducing T cell death or apoptosis. Fas mediates apoptosis of recently activated T cells which are again exposed to stimulation (van Parijs et al., Immunity 4: 321-328 (1996)). Fas is a type I membrane receptor that when crosslinked by its cognate ligand induces apoptosis in a wide variety of cells. The interaction between the Fas molecule (CD95) on target T cells and its ligand Fas L on mesenchymal stem cells results in receptor aggregation, which transduces signals leading to apoptosis of the target cell. The Fas system has been shown to be involved in a number of cell functions in vivo including negative selection of thymocytes, maintaining immune privilege sites within the body, and cytotoxic T-lymphocyte (CTL)-mediated cytotoxicity (Green and Ware, Proc Natl Acad Sci, 94(12):5986-90 (1997)).

Other members of the tumor necrosis factor receptor (TNFR) family have roles in programmed cell death. TRAIL ligand, which interacts with its receptor DR4 can induce apoptosis in a variety of transformed cell lines (G. Pan et al. Science, 277:815-818 (1997)); and the expression of CD27 and its ligand CD70 (Prasad et al., Proc Natl Acad Sci, 94:6346-6351 (1997)) also induces apoptosis. Fas expression is restricted to stimulated T cells and sites of immune privilege. TRAIL is detected in many normal tissues.

Both Trail-ligand and CD27, but not Fas-ligand, are expressed on unmanipulated human mesenchymal stem cells. Activated, but not resting, T cells express the Trail receptor and CD70. Most of the T cells found in the body are in the resting state; T cells are activated when they encounter cells both in the context of MHC and the appropriate co-stimulatory molecule such as B7-1 or B7-2.

Thus, the engagement of cell death receptors on activated T cells with their ligands expressed on the mesenchymal stem cells results in T cell death via apoptosis. Ligands and their receptors other than those specifically mentioned above, either present within the mesenchymal stem cell or introduced into the mesenchymal stem cell can perform this function. Therefore, mesenchymal stem cells administered to an individual delete activated T cells, reducing the severity or incidence of transplant rejection disease.

The dose of the dermal mesenchymal stem cells varies within wide limits and will, of course be fitted to the individual requirements in each particular case. The number of cells used will depend on the weight and condition of the recipient and other variables known to those of skill in the art.

The cells can be administered by a route which is suitable for the particular tissue or organ to be treated. Modes of administration of the mesenchymal stem cell preparation include but are not limited to systemic intravenous injection and injection directly to the intended site of activity. The preparation can be administered by any convenient route, for example by infusion or bolus injection and can be administered together with other biologically active agents. Administration is preferably systemic, i.e., parenterally, by intravenous injection. In some cases, the dermal mesenchymal stem cells are delivered to the site of desired treatment or therapy and can be targeted to a particular tissue or organ.

In general, in the case of parenteral administration, it is customary to administer from about 0.01 to about 5 million cells per kilogram of recipient body weight. The number of cells used will depend on the weight and condition of the recipient, the number of or frequency of administrations, and other variables known to those of skill in the art. The mesenchymal stem cells can be administered by a route which is suitable for the tissue, organ or cells to be transplanted. They can be administered systemically, i.e., parenterally, by intravenous injection or can be targeted to a particular tissue or organ, such as bone marrow. The human mesenchymal stem cells can be administered via a subcutaneous implantation of cells or by injection of stem cell into connective tissue, for example muscle.

The cells can be suspended in an appropriate diluent, at a concentration of from about 0.01 to about $5 \times 10^6$ cells/ml. Suitable excipients for injection solutions are those that are biologically and physiologically compatible with the cells and with the recipient, such as buffered saline solution or other suitable excipients. The composition for administration must be formulated, produced and stored according to standard methods complying with proper sterility and stability. Other excipients include water, isotonic common salt solutions, alcohols, polyols, glycerine and vegetable oils. The composition for administration must be formulated, produced and stored according to standard methods complying with proper sterility and stability.

The mesenchymal stem cell can be administered alone, however in a preferred embodiment, the mesenchymal stem cells are utilized in the form of pharmaceutical compositions. Such compositions comprise a therapeutically effective amount of the dermal mesenchymal stem cells, and a pharmaceutically acceptable carrier or excipient. Such a carrier includes but is not limited to saline, buffered saline, dextrose, water, and combinations thereof.

In a preferred embodiment, the mesenchymal stem cell preparation or composition is formulated in accordance with routine procedures as a pharmaceutical composition adapted for intravenous administration to human beings. Typically, compositions for intravenous administration are solutions in sterile isotonic aqueous buffer. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also includes prefilled pharmaceutical containers (e.g., injection vials, ampoules, infusion bags etc.) containing a unit dose of cells (i.e., the number of cells to be given at a single time to a patient). The cells may be suspended in a solution (e.g., sterile isotonic saline) together with agents that help in their preservation (e.g., glycerol). Other agents such as antibiotics, pharmaceutically acceptable salts, buffers and excipients may also be included. The prefilled pharmaceutical containers in unit dose form may be kept refrigerated or stored frozen. They may also be supplied as part of a kit that has instructions for the administration of the cells to transplant patients or patients with an autoimmune disease.

The present invention also provides any of the above-mentioned compositions in kits, optionally including instructions for use of the composition for the treatment of a condition described herein. That is, the kit can include a description of use of the composition for participation in any biological or chemical mechanism disclosed herein. The kits can further include a description of activity of the condition in treating the pathology, as opposed to the symptoms of the condition.

That is, the kit can include a description of use of the compositions as discussed herein. The kit also can include instructions for use of a combination of two or more compositions of the invention, or instruction for use of a combination of a composition of the invention and one or more other compounds indicated for treatment of the diseases. Instructions also may be provided for administering the composition by any suitable technique as previously described, for example, orally, intravenously, pump or implantable delivery device, or via another known route of drug delivery. The kits may also be one or more reagents associated with the isolation and purification for the dermal mesenchymal stem cells, i.e. ABCB5 antibodies, and instructions for isolating and/or purifying the cells.

The kits described herein may also contain one or more containers, which may contain the composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

EXAMPLES

Example 1

A. ABCB5 Marks Murine Dermal MSC

Human ABCB5 P-glycoprotein marks MSC phenotype-expressing stem cell subpopulations in physiological skin and malignant melanomas (Frank, et. al., *J. Biol. Chem.* 278: 47156 (2003); Frank, et. al., *Cancer Res.* 65:4320 (2005)). Murine ABCB5, which was found in transfection experiments to be recognized by the anti-ABCB5 mAb 3C2-1D12 directed against a species-conserved extracellular epitope of the molecule (Frank, et. al., *J. Biol. Chem.* 278:47156 (2003)), marks identical dermal MSC subpopulations, as determined by HRP-immunoenzymatic staining for ABCB5, when frozen tissue sections across the anastomosis of human to SCID mouse skin xenografts were compared.

B. Cloning and Characterization of ABCB5+ Dermal Mesenchymal Stem Cells

A protocol was developed to study the immunomodulatory properties of murine ABCB5+ dermal MSC. The protocol included isolating, cloning, propagating, and expanding this stem cell population in vitro under defined, previously described medium conditions (Frank, et. al., *J. Biol. Chem.* 278:47156 (2003)). Briefly, murine skin was harvested from adult (6-10 weeks old) Balb/c or C57BL/6 strain mice (C57BL/6 (H-$2^b$) and BALB/c (H-$2^d$) wild-type mice were obtained from Taconic Farms, Germantown, N.Y.), dissected into small pieces and dissociated with collagenase, followed by isolation of ABCB5+ cells using anti-ABCB5 mAb, goat anti-mouse Ig-coated magnetic microbeads and MiniMACS separation columns, and subsequent cell cloning by limiting dilution. Surface expression of murine ABCB5 was determined in clonally-derived successive cell passages using immunofluorescence staining with anti-ABCB5 mAb and flow cytometry (FIGS. 1A, B).

Figure 1B:
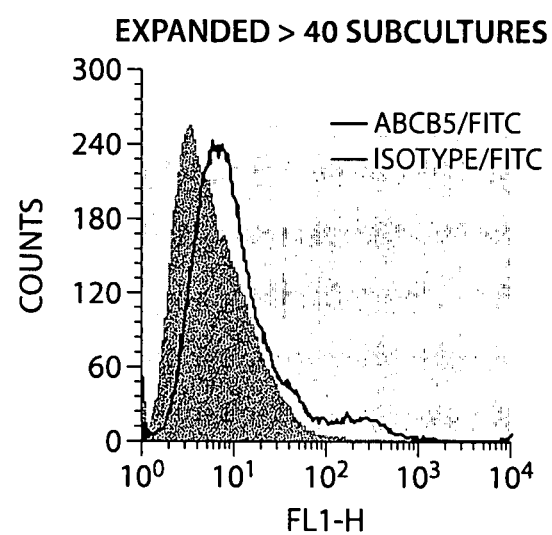
Figure 2:
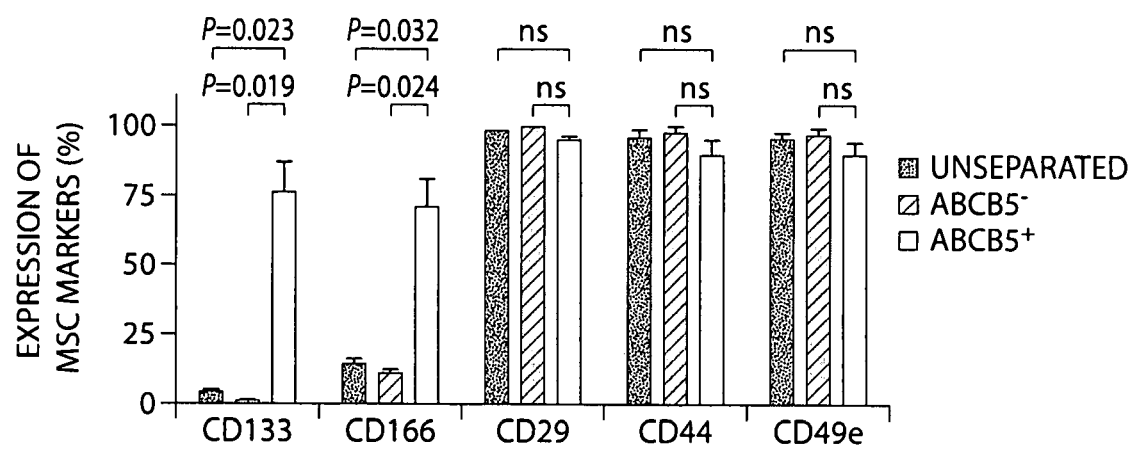

While ABCB5 was expressed in early passages by the majority of cells (FIG. 1A), we found ABCB5 expressed by 5-15% of cells in successive single cell-derived cultures (FIG. 1B), indicating that ABCB5+ stem cells give rise in culture to more differentiated, ABCB5− progeny. ABCB5+ dermal cells nevertheless maintained constant relative abundance ratios vis-à-vis ABCB5− bulk populations during long-term culture expansion, demonstrating self-renewal capacity of this cell subset. Further phenotypic characterization of murine Balb/c single cell-derived cultures revealed significant expression of the MSC-associated markers CD29 (98.1−/+0.1%; mean−/+SD), CD44 (95.6−/+4.7%), CD49e (95.2−/+3.5%), CD166 (14.5−/+2.4%), and CD133 (4.0−/+1.4%) among all cells, even in later passages (>30, n=3), with preferential expression of the most primitive stem cell markers CD133 and CD166 noted on ABCB5+ compared to ABCB5− subpopulations (76.4−/+18.5% vs. 0.7−/+0.9% and 70.7−/+17.9% vs. 10.8−/+2.8%, respectively; mean−/+SD) (FIG. 2). Clonally-derived ABCB5+ dermal MSC were found to possess multipotent differentiation potential, further indicative of their MSC phenotype, under distinct culture conditions in vitro, with a capacity to generate myosin heavy chain-expressing multinucleated myocytes, osteocytes, and adipocytes, when stained with appropriate lineage markers (FITC-conjugated anti-myosin heavy chain mAb, Alizarin Red S staining, Oil Red staining, respectively).

Example 2

Immunomodulatory Effect of ABCB5 Positive Dermal MSC

Figure 3A:
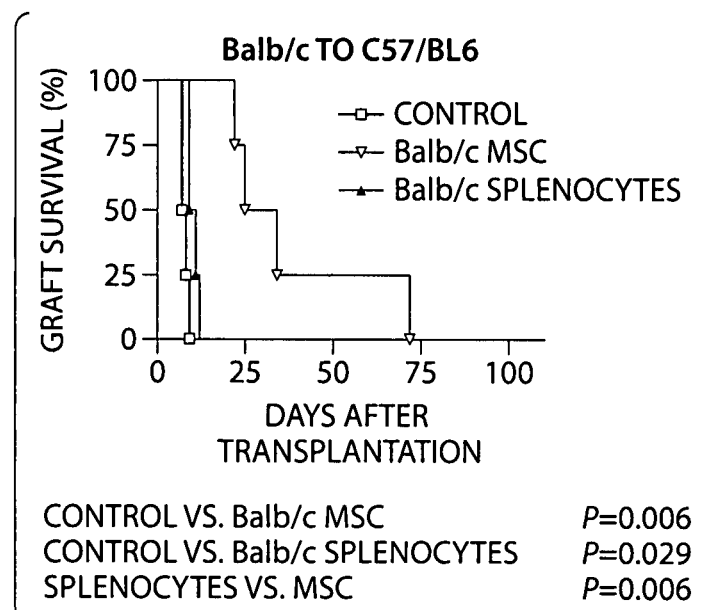
FIG. 3. Kaplan-Meier graphs depicting graft survival in (A) donor-derived MSC-treated B6 recipients of Balb/c donor hearts, and (B) with and without concurrent blockade of CD40L, using the anti-CD40L mAb, MRI. (C) Kaplan-Meier graphs depicting graft survival in third-party derived MSC-treated B6 recipients of C3H donor hearts, and in (D) recipient-derived MSC-treated Balb/c recipients of B6 donor hearts. Statistical differences as indicated by P values for each strain combination were assessed using the log-rank test.

A. The immunomodulatory function of clonal ABCB5+-derived dermal MSC was studied in vivo, using a murine heterotopic cardiac allotransplantation model as previously described (Yamada, et al., *J. Immunol.* 167:140 (2001)). In a fully mismatched strain combination, treatment of C57BL/6 recipients of Balb/c cardiac allografts with donor-type dermal MSC ($3 \times 10^6$ cells i.v., day-7) resulted in significant prolongation of allograft survival compared to donor-type splenocyte-treated or untreated control recipients (median graft survival 29.5 days vs. 10 days (P=0.012) or 7.5 days (P=0.006), respectively), (FIG. 3A) demonstrating the in vivo efficacy of dermal MSC to delay graft rejection.

Figure 3B:
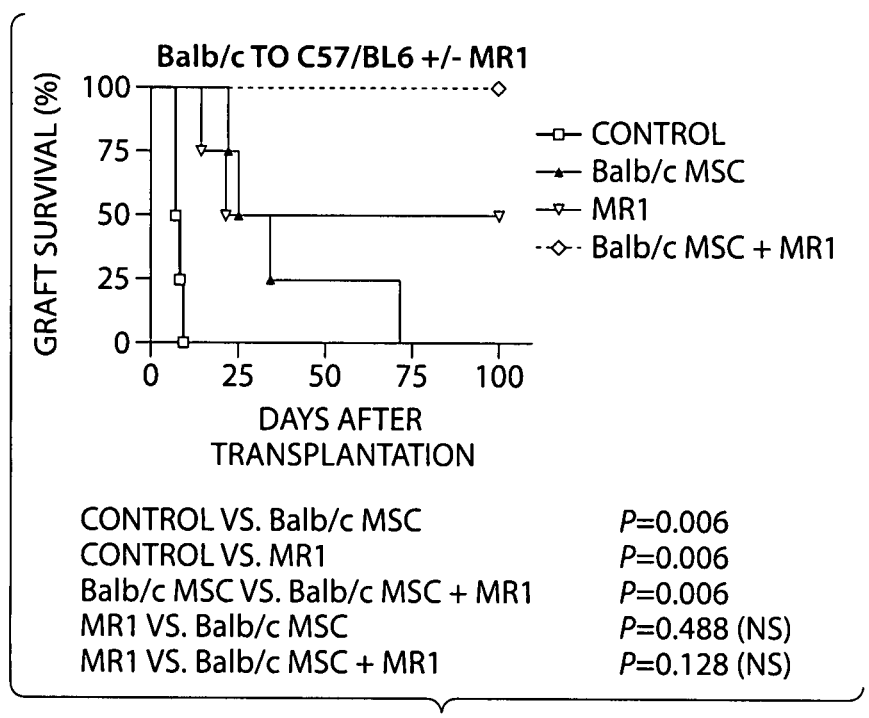
Figure 3C:
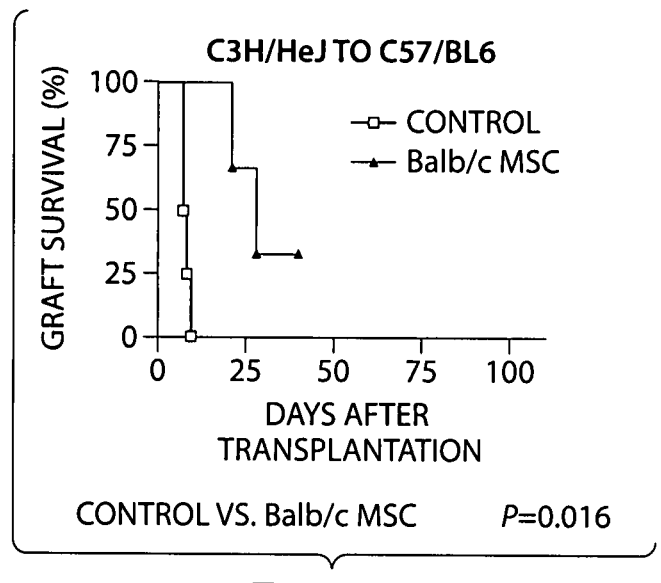
Figure 3D:
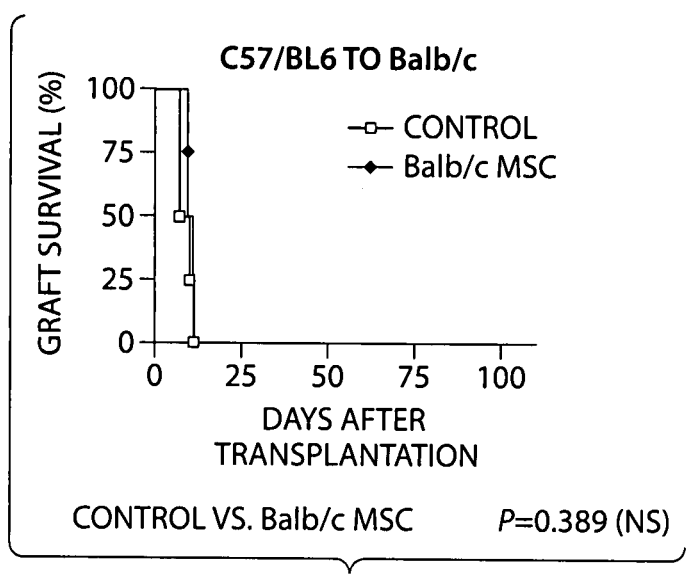

B. Long-term allograft survival >100 days was achieved in n=4/4 animals when dermal MSC treatment was combined with CD40L-directed costimulatory blockade using the anti-CD40L mAb MR1 (250 mg/kg i.p. q.o.d. from day 0-10) as previously described (Ozkaynak, et al., *J. Immunol.* 169:6546 (2002); Kishimoto, et al., *J. Clin. Invest.* 106:63 (2000)) (FIG. 3B). Third-party, Balb/c strain dermal MSC also prolonged cardiac allograft survival in C57BL/6 recipients of C3H/HeJ hearts compared to untreated controls (median graft survival 28 days vs. 7.5 days, P=0.016) (FIG. 3C). Balb/c recipients of C57BL/6 heart allografts treated with recipient-strain MSC, however, rejected donor hearts with the same tempo as untreated control mice (FIG. 3D). The results suggest that administration of MSC for prolongation of allograft survival is most effective under these conditions in the presence of a stem cell-dependent allogeneic stimulus. However, this does not rule out activity under more stringent conditions with non-allogeneic cells.

Example 3

ABCB5+ Dermal MSC Coexpress PD-1 and Upon Allotransplantation Activate Expression of the PD-1 Ligand PD-L2 on Recipient T Cells In Vivo The PD-1-(PD-L1/PD-L2) negative costimulatory pathway has recently been implicated in BM-MSC-mediated immune regulation in vitro (Augello, et al., *Eur. J. Immunol.* 35:1482 (2005)). The mechanism underlying dermal MSC-mediated prolongation of cardiac allograft survival, was addressed by systematically analyzing expression of known costimulatory receptors and their ligands (Rothstein, et al., *Immunol. Rev.* 196:85 (2003)) on Balb/c ABCB5+-derived dermal MSC.

Figure 4A:
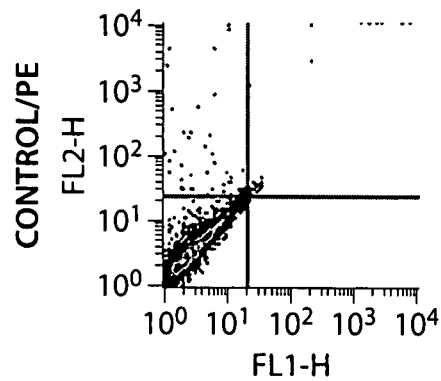
FIG. 4. Dot plots depicting dual color flow cytometry analysis of murine Balb/c skin-derived cultures for ABCB5 expression (FITC, FL1 fluorescence) and for the PD-1, PD-L1, and PD-L2 markers (PE, FL2 fluorescence). ABCB5⁺ cells coexpressing the respective surface markers are found in the top right quadrant of each fluorescence plot.
Figure 4B:
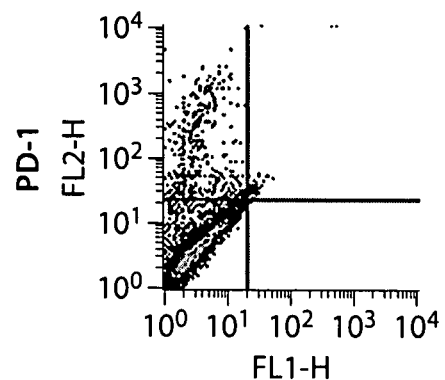
Figure 4C:
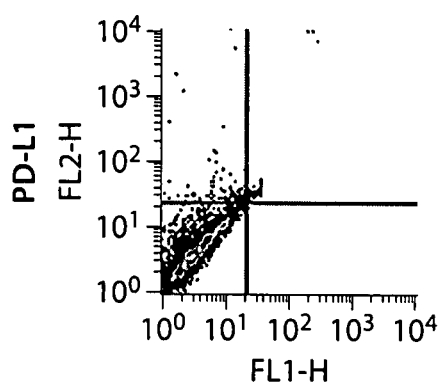
Figure 4D:
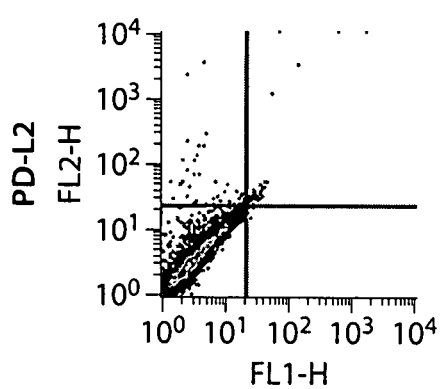
Figure 4E:
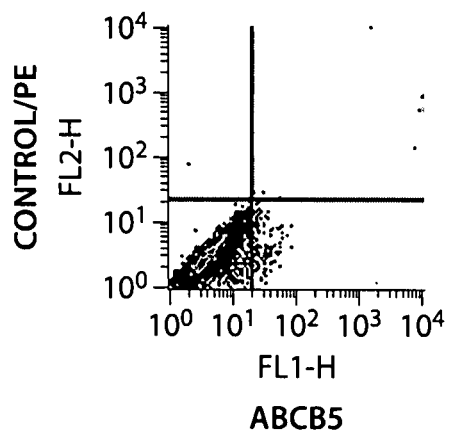
Figure 4F:
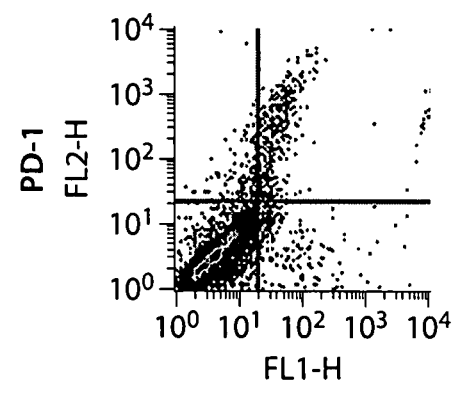
Figure 4G:
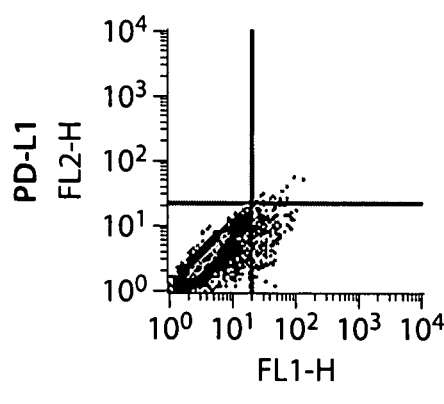
Figure 4H:
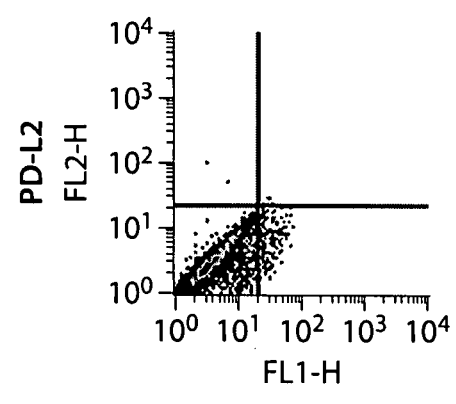
Figure 5A:
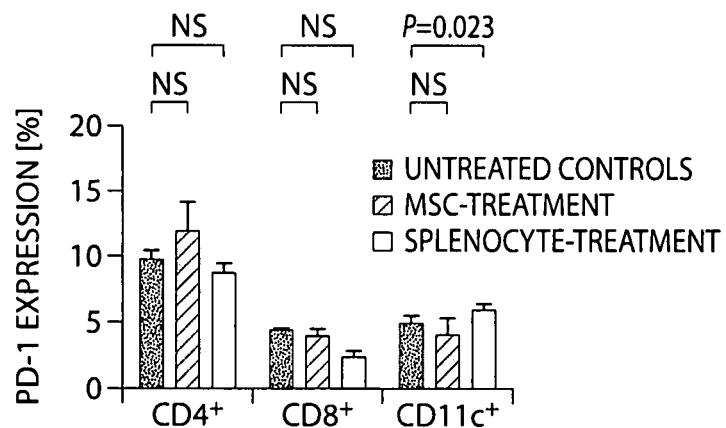
FIG. 5. Bar graphs depicting the expression of PD-1, PD-L1, and PD-L2 on fully-mismatched recipient CD4⁺, CD8⁺, and CD11c⁺ cells in vivo 7 days after allo-transplantion of $3\times10^6$ MSC, determined by flow cytometry. Untreated controls (solid bars), MSC-treatment (dotted bars), splenocyte treatment (striped bars); NS: not significant; p-value(s) indicate statistically significant changes FIG. 6. Bar graph depicting CD40 expression (% positivity, mean±SEM) determined by dual color flow cytometry on CD11c⁺ APC splenocyte subsets derived from spleens of either MSC-treated (7 days post i.v. injection of $3\times10^6$ ABCB5⁺ dermal MSC) (gray bar, labeled MSC Treatm.) or untreated control animals (black bar, labeled No Treatm.). B and C. Graphs depicting $^3$H-thymidine uptake of T cells purified from ABCB5⁺ dermal MSC-treated (7 days post i.v. injection of $3\times10^6$ ABCB5⁺ dermal MSC) or untreated C57BL6 mice, upon allostimulation for 120 hours in standard one-way mixed lymphocyte reactions (MLR) with irradiated (1750 rad) naïve Balb/c (B) or C3H/HeJ (C) splenocytes.
Figure 5B:
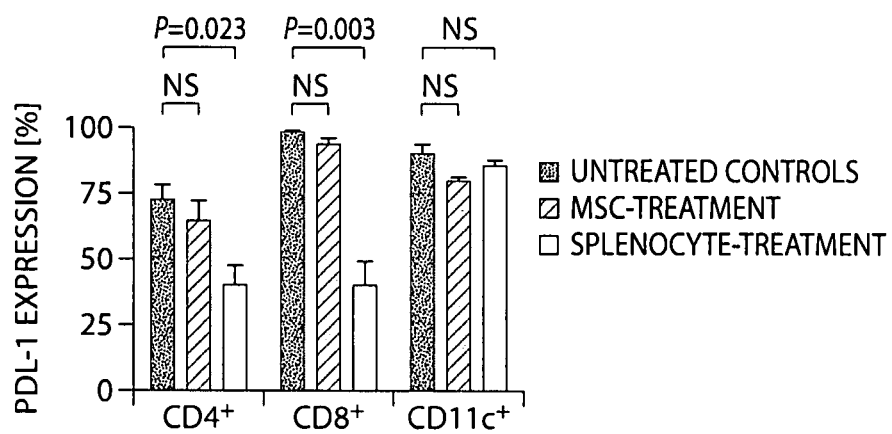
Figure 5C:
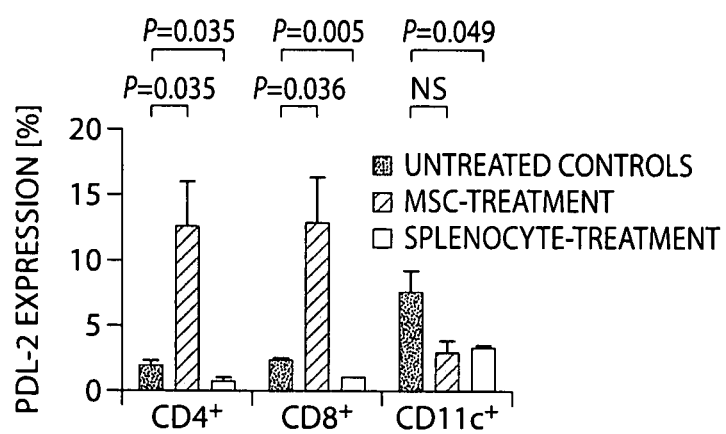

Out of >20 costimulatory molecules examined, immunofluorescence double staining and flow cytometry revealed specific coexpression of ABCB5 with the negative costimulatory molecule PD-1, (FIG. 4F) but not its ligands, PD-L1 (FIG. 4G) and PD-L2 (FIG. 4H), which are not expressed by dermal MSC, and compared to the controls (FIGS. 4A, E, B-D). No significant expression of positive costimulatory molecules was detected. Examination of in vivo costimulatory molecule expression on peripheral immune cells of C57BL/6 recipients 7 days following i.v. injection of $3\times10^6$ allogeneic Balb/c dermal MSC, before cardiac allotransplantation, revealed that dermal MSC treatment had specifically and significantly ($P<0.01$) activated expression of the PD-1 ligand PD-L2 on 12.5+/−3.8% of recipient CD4+ T cells (mean+/−SD) and 12.9+/−2.4% of recipient CD8+ T cells, but not on recipient CD11c+ APCs, when compared to Balb/c splenocyte-treated or naïve control animals (FIG. 5C). Moreover, recipient T cell expression of the PD-1 ligand PD-L1 was preserved in dermal MSC-treated animals, unlike in allogeneic Balb/c splenocyte-treated mice, where PD-L1 expression was markedly down-regulated (FIG. 5B). No differential expression pattern of PD-1 on recipient immune cells was detected (FIG. 5A).

These findings suggest that the immunosuppressive effect of ABCB5+ dermal MSC in allotransplantation is closely tied to specific coexpression of the negative costimulator PD-1. Furthermore, dermal MSC-mediated specific induction of PD-L2 expression on recipient T cells suggest a functional role of these not previously recognized cell populations in the prolongation of cardiac allograft survival.

Example 4

In Vivo Immunomodulatory Function of ABCB5+ Murine Dermal MSC.

Figure 6A:
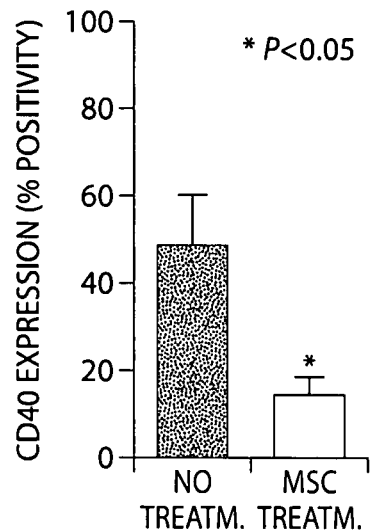
Figure 6B:
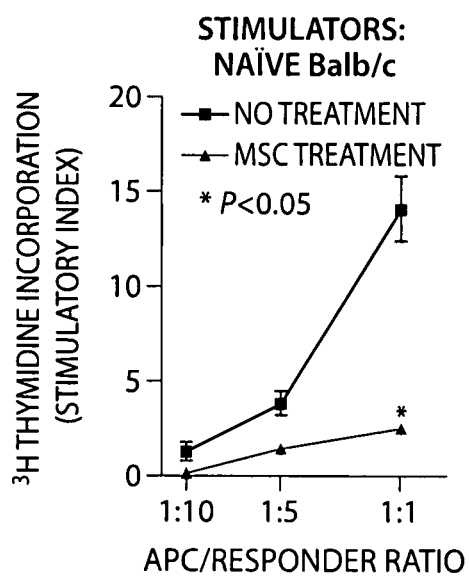
Figure 6C:
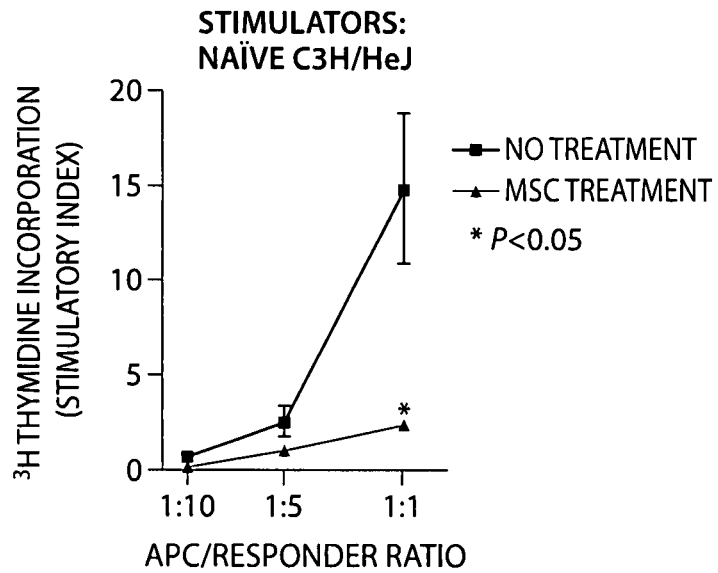
Figure 6D:
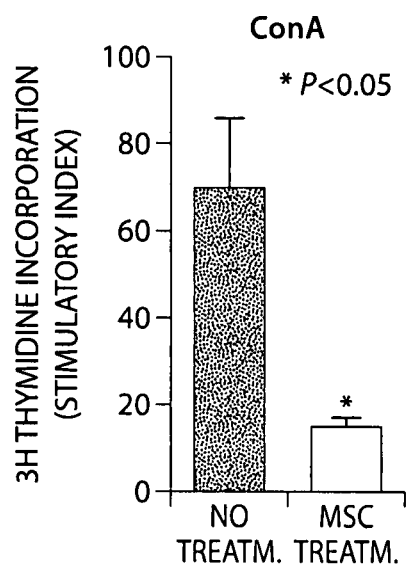

When $3\times10^6$ autologous, clonally-derived murine ABCB5+ dermal MSC were intravenously (i.v.) grafted to C57/BL6 mice, ABCB5+ dermal MSC administration resulted in a 3.4-fold reduction in surface expression of the costimulatory pathway member CD40 on CD11c+ APCs isolated 7 days post transplantation from spleens of MSC-treated animals compared to CD11c+ APCs derived from untreated controls (48.71±11.43% vs. 14.34±4.53%, $P<0.05$, mean±SEM) (FIG. 6A), indicating that in vivo transplantation of ABCB5+-derived dermal MSC can inhibit an APC-expressed positive costimulatory signal critically involved in T cell activation. T cells derived from autologous MSC-treated animals exhibited significantly impaired proliferation compared to those derived from untreated controls, to either allogeneic stimulation in standard one-way mixed lymphocyte reactions (MLR) with irradiated naïve Balb/c or C3H/HeJ splenocytes (inhibition 82%±9% for Balb/c stimulators and 84%±5% for C3H/HeJ stimulators at 1:1 stimulator to responder ratios, mean±SD, $P<0.001$, respectively) (FIGS. 6B and 6C), or to mitogenic stimulation with ConA (FIG. 6D). These findings show that ABCB5+ murine dermal MSC can exert distinct modulatory effects on both APC maturation and T cell activation in vivo.

All references cited herein are fully incorporated by reference. Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of obtaining an isolated substantially pure preparation of ABCB5 positive immunomodulatory dermal mesenchymal stem cells comprising:
   a) obtaining a sample of dermal tissue that has been separated from epidermal tissue from a human donor;
   b) isolating ABCB5 positive cells from the dermal tissue sample, wherein the ABCB5 positive cells are isolated using immobilized antibody against ABCB5
   c) expanding the ABCB5 positive cells by limiting dilution cloning to produce the isolated substantially pure preparation of ABCB5 positive immunomodulatory dermal mesenchymal stem cells, and
   d) formulating the ABCB5 positive cells in a pharmaceutically acceptable carrier for administration to a human subject, wherein ABCB5 positive dermal cells comprise at least 95% of the isolated substantially pure preparation of ABCB5 positive immunomodulatory dermal mesenchymal stem cells.

2. An isolated substantially pure preparation of immunomodulatory dermal mesenchymal stem cells characterized by the expression of ABCB5 on their cell surface formulated in a pharmaceutically acceptable carrier or excipient that is a sterile isotonic buffer, wherein the cells are isolated according to the method of claim 1, and wherein ABCB5 positive dermal cells comprise at least 95% of the isolated substantially pure preparation of ABCB5 positive immunomodulatory dermal mesenchymal stem cells.

3. The isolated preparation of claim 2, wherein the isolated preparation of immunomodulatory dermal mesenchymal stem cells further comprises a local anesthetic.

4. A prefilled injection vial, ampoule or infusion bag comprising, in unit dose form, the isolated dermal mesenchymal stem cells of claim 2.

5. The injection vial, ampoule or infusion bag of claim 4, wherein the injection vial or infusion bag comprises $1\times10^7$-$1\times10^{10}$ of the dermal mesenchymal stem cells.

6. The injection vial, ampoule or infusion bag of claim 5, wherein the injection vial, ampoule or infusion bag comprises $1\times10^8$-$5\times10^9$ of the dermal mesenchymal stem cells.

7. A kit comprising the prefilled injection vial, ampoule or infusion bag of either claim 5 or 6 together with instructions on the administration of the dermal mesenchymal stem cells to either a subject that has undergone or is about to undergo an organ transplant, a subject having an autoimmune disease, a liver disease, a neurodegenerative disease, or a cardiovascular disease.

8. The isolated preparation of claim 2, further comprising a biologically active agent.

9. The isolated preparation of claim 8, wherein the biologically active agent is an agent for the treatment of a disorder selected from the group consisting of an autoimmune disease, a liver disease, a neurodegenerative disease, and a cardiovascular disease.

10. The isolated preparation of claim 8, wherein the biologically active agent is an exogenous genetic material.

\* \* \* \* \*